US011872271B2

(12) United States Patent
Murakami et al.

(10) Patent No.: US 11,872,271 B2
(45) Date of Patent: Jan. 16, 2024

(54) HIGH-AFFINITY ANTI-VEGF ANTIBODY KLHA505

(71) Applicants: ORDER-MADE MEDICAL RESEARCH INC., Tsukuba (JP); SANTEN PHARMACEUTICAL CO., LTD., Osaka (JP)

(72) Inventors: Yasufumi Murakami, Chiba (JP); Shigeki Mukoubata, Chiba (JP); Hirotada Akiyama, Chiba (JP); Koji Konomi, Nara (JP)

(73) Assignees: ORDER-MADE MEDICAL RESEARCH INC., Tsukuba (JP); SANTEN PHARMACEUTICAL CO., LTD., Osaka (JP)

(*) Notice: Subject to any disclaimer, the term of this patent is extended or adjusted under 35 U.S.C. 154(b) by 31 days.

(21) Appl. No.: 17/229,271

(22) Filed: Apr. 13, 2021

(65) Prior Publication Data

US 2021/0228700 A1 Jul. 29, 2021

Related U.S. Application Data

(63) Continuation of application No. 16/067,931, filed as application No. PCT/JP2017/000101 on Jan. 5, 2017, now Pat. No. 11,007,259.

(30) Foreign Application Priority Data

Jan. 6, 2016 (JP) ................. 2016-001277

(51) Int. Cl.
*A61K 39/00* (2006.01)
*A61P 35/00* (2006.01)
*C07K 16/22* (2006.01)

(52) U.S. Cl.
CPC ...... *A61K 39/001135* (2018.08); *A61P 35/00* (2018.01); *C07K 16/22* (2013.01); *A61K 2039/505* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2002/0119153 A1 | 8/2002 | Thorpe et al. |
| 2005/0106667 A1 | 5/2005 | Fellouse et al. |
| 2008/0213268 A1 | 9/2008 | Watts et al. |
| 2010/0061988 A1 | 3/2010 | Hansen |
| 2010/0111967 A1 | 5/2010 | Baehner et al. |
| 2010/0150919 A1 | 6/2010 | Appleton et al. |
| 2011/0097340 A1 | 4/2011 | Ramachandra et al. |
| 2012/0014958 A1 | 1/2012 | Borras et al. |
| 2012/0231011 A1 | 9/2012 | Ll et al. |
| 2014/0170137 A1 | 6/2014 | Gearing |
| 2015/0315270 A1 | 11/2015 | Baldi et al. |
| 2016/0122426 A1 | 5/2016 | Doh et al. |
| 2017/0015742 A1 | 1/2017 | Gu et al. |

FOREIGN PATENT DOCUMENTS

| | | |
|---|---|---|
| EP | 0419858 A1 | 4/1991 |
| EP | 3006465 A1 | 4/2016 |
| JP | 2002-543093 A | 12/2002 |
| JP | 2007-528756 A | 9/2007 |
| JP | 2010-530359 A | 9/2010 |
| JP | 2011-500086 A | 1/2011 |
| JP | 2011-525359 A | 9/2011 |
| JP | 2011-256183 A | 12/2011 |
| JP | 2012-504943 A | 3/2012 |
| JP | 2013-502445 A | 1/2013 |
| JP | 2014-516026 A | 7/2014 |
| WO | WO 2007/047626 A1 | 4/2007 |
| WO | WO 2014/193191 A1 | 12/2014 |
| WO | WO 2015/166112 A1 | 11/2015 |
| WO | WO 2016/205427 A2 | 12/2016 |

OTHER PUBLICATIONS

Liu et al., "The expression of VEGF, bFGF and MVD in human malignant melanoma and their clinicopathological significance," J Clin Dermatol, vol. 35, No. 7, Jul. 2006, pp. 433-435 with English abstract.

Beck et al., "A Vascular niche and a VEGF-Nrpl loop regulate the initiation and stemness of skin tumours", Nature, vol. 478, Oct. 20, 2011, pp. 399-403 (7 pages).

Carmeliet et al., "Common Mechanisms of nerve and blood vessel wiring", Nature, vol. 436, No. 14, Jul. 2005, pp. 193-200 (8 pages).

Doi et al., "S7-5 Clinical Applications of Molecular Target Inhibitors Through VEGF/VEGFR (Focusing on Antibody Medicine)", The 45th Congress of Japan Society for Cancer Therapy, vol. 42, No. 2, Sep. 20, 2007, pp. 249 with abstract.

Ferrara et al., "The Biology of Vascular Endothelial Growth Factor", Endocrine Reviews, vol. 18, No. 1, Feb. 1997, pp. 4-25 (22 pages).

Graziani et al., "Neuropilin-1 as therapeutic target for malignant melanoma", Frontiers in Oncology, vol. 5, Article 125, Jun. 2015, pp. 1-9 (9 pages).

Harper et al., "VEGF-A Splicing: the key to anti-angiogenic therapeutics", Nat Rev Cancer. Author Manuscript, vol. 8, No. 11, Nov. 2008, pp. 880-887 (17 pages).

Heskamp et al., "Bevacizumab reduces tumor targeting of antiepidermal growth factor and anti-insulin growth factor 1 receptor antibodies", Int. J. Cancer, vol. 133, 2013, pp. 307-314 (8 pages).

(Continued)

*Primary Examiner* — Christine J Saoud
(74) *Attorney, Agent, or Firm* — Birch, Stewart, Kolasch & Birch, LLP

(57) ABSTRACT

An object of the present invention is to provide an antibody having significantly high affinity for VEGF compared to the prior art. The present invention provides a monoclonal antibody against VEGF, which binds to a vascular endothelial growth factor (VEGF) with a dissociation constant of $1 \times 10^{-11}$ mol/L or less.

21 Claims, 8 Drawing Sheets

Specification includes a Sequence Listing.

(56) References Cited

OTHER PUBLICATIONS

Jones et al., "Separating genetic and hemodynamic defects in neuropilin 1 knockout embryos", Development, vol. 135, 2008, pp. 2479-2488 (10 pages).

Keyt et al., "Identification of Vascular Endothelial Growth Factor Determinants for Binding KDR and FLT-1 Receptors", The Journal of Biological Chemistry, vol. 271, No. 10, 1996, pp. 5638-5646 (10 pages).

Khadidja-Tehami et al., "Production of polyclonal anti VEGF antibodies and establishment of sELISA system for detection of serum VEGF level in tumor patients", Journal of Chemical and Pharmaceutical Research, vol. 7, No. 6, 2015, pp. 672-679 (8 pages).

Marti et al., "Angioenesis in Ischemic Disease", Thromb Haemost, vol. 82, 1999, pp. 44-52 ( 9 pages).

Matsumoto et al., "VEGF Receptor Signal Transduction", Science's stke, URL: www.stke.org/cgi/content/full/OC_sigtrans;2001/112/re21, 2011, pp. 1-17 (17 pages).

Pan et al., "Blocking Neuropilin-1 Funtion Has an Additve Effect with Anti-VEGF to Inhibit Tumor Growth", Cancer Cell, vol. 11, Jan. 2007, pp. 53-67 ( 15 pages).

Parker et al., "Structural Basis for Selective Vascular Endothelial Growth Factor-A (VEGF-A) Binding to Neuropilin-1", The Journal of Biological Chemistry, vol. 287, No. 14, Mar. 30, 2012, pp. 11082-11089 (8 pages).

Schlaeppi et al., "Characterization of a new potent, in vivo neutralizing monoclonal antibody to human vascular endothelial growth factor", J. Cancer Res Clin Oncol, vol. 125, 1999, pp. 336-342 ( 7 pages).

Sela-Culang et al., Fron. Immunol. 4(302): 1-13, 2013.

Soker et al., "Neuropilin-1 Is Expressed by Endothelial and Tumor Cells as an Isoform-Specific Receptor and Vascular Endothelial Growth Factor", Cell, vol. 92, Mar. 20, 1998, pp. 735-745 (11 pages).

Stewart, "Aflibercept as a Treatment for Age-Related Macular Degeneration", US Opthalimic Rev. vol. 6, 2013, pp. 58-63 ( 6 pages).

Sullivan et al., "r84, a Novel Therapeutic Antibody against Mouse and Human VEGF with Potent Anti-Tumor Activity and Limited Toxicity Induction", Plos One, vol. 5, Issue 8, Aug. 2010, pp. 1-13 (13 pages).

Tugues et al., "Vascular endothelial growth factors and receptors: Anti-angiogenic therapy in the treatment of cancer", Molecular Aspects of Medicine, vol. 32, 2011, pp. 88-111 (24 pages).

Yu et al., "A Humanized Anti-VEGF Rabbit Monoclonal Antibody Inhibits Angiogenesis and Blocks Tumor Growth in Xenograft Models", PloS ONE, vol. 5, Issue 2, Feb. 2010, pp. 1-12 (12 pages).

[Figure 1]
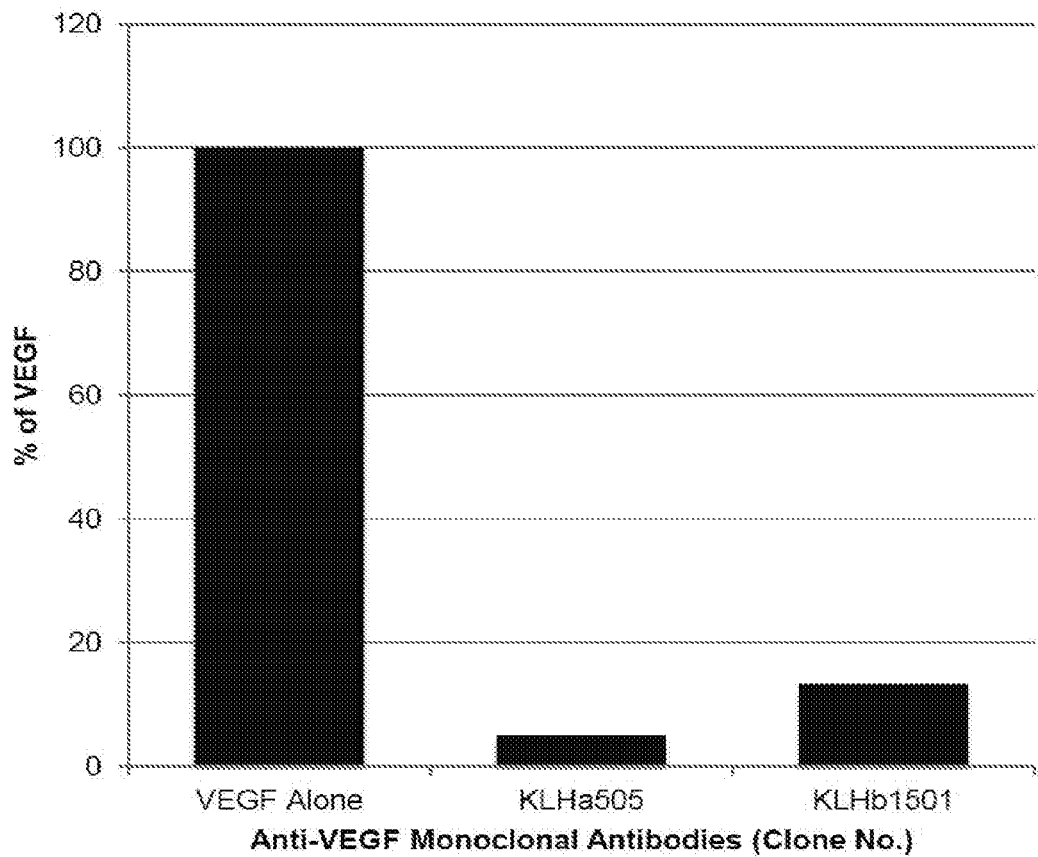

[Figure 2]
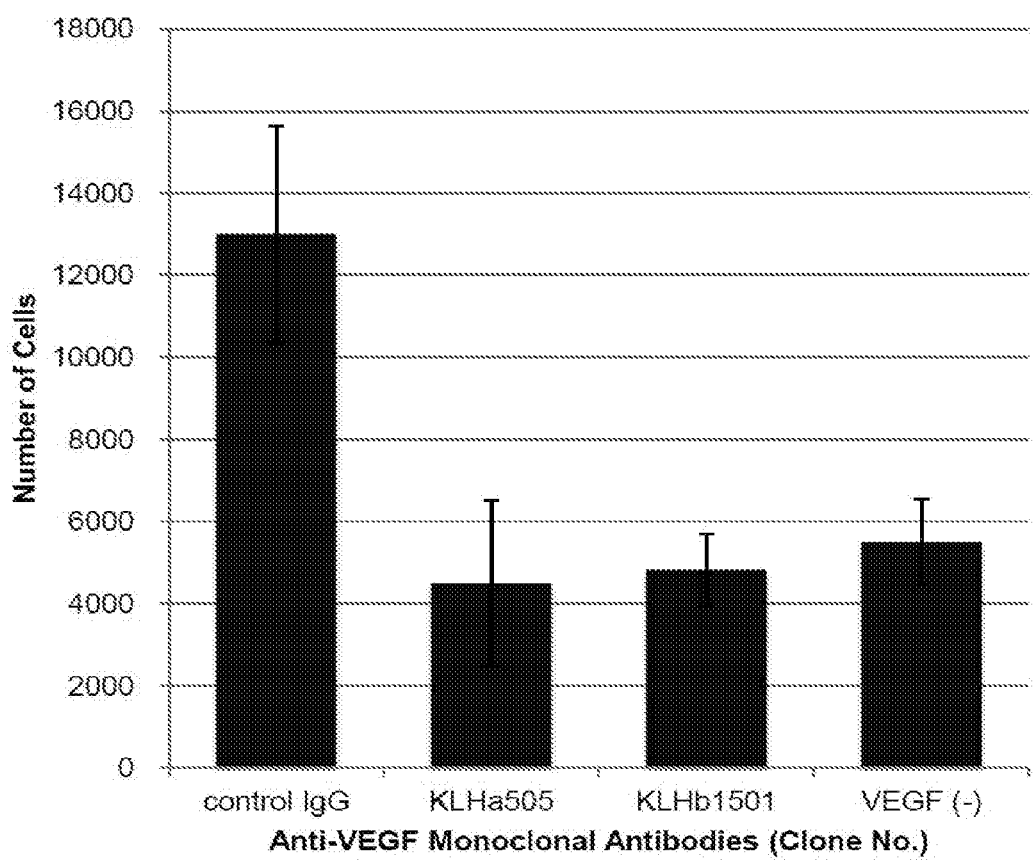

[Figure 3]
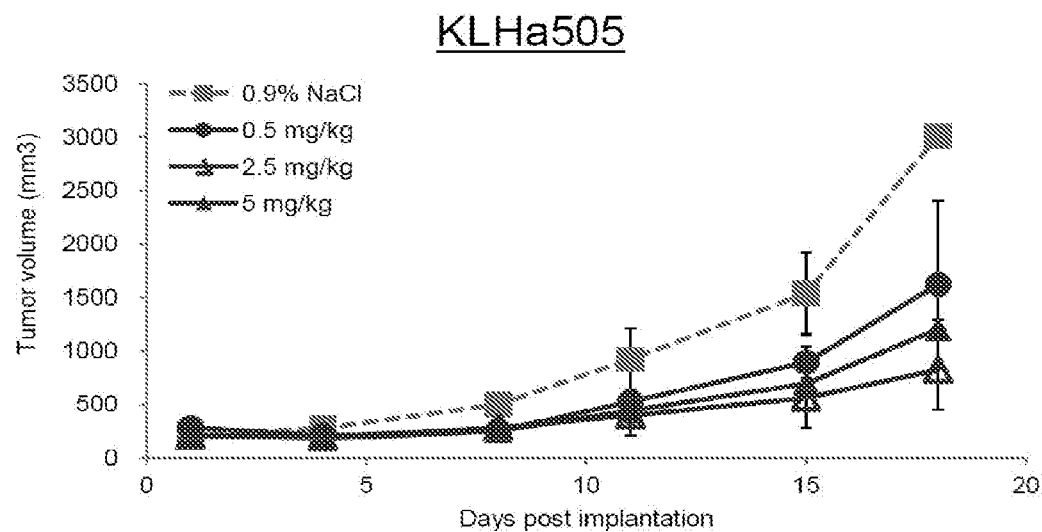
[Figure 4]
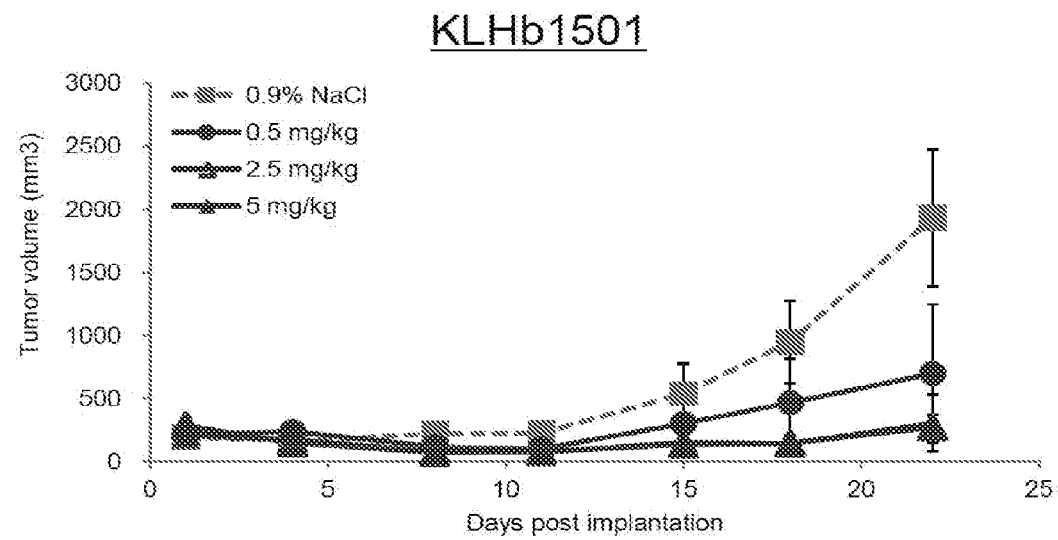

[Figure 5]
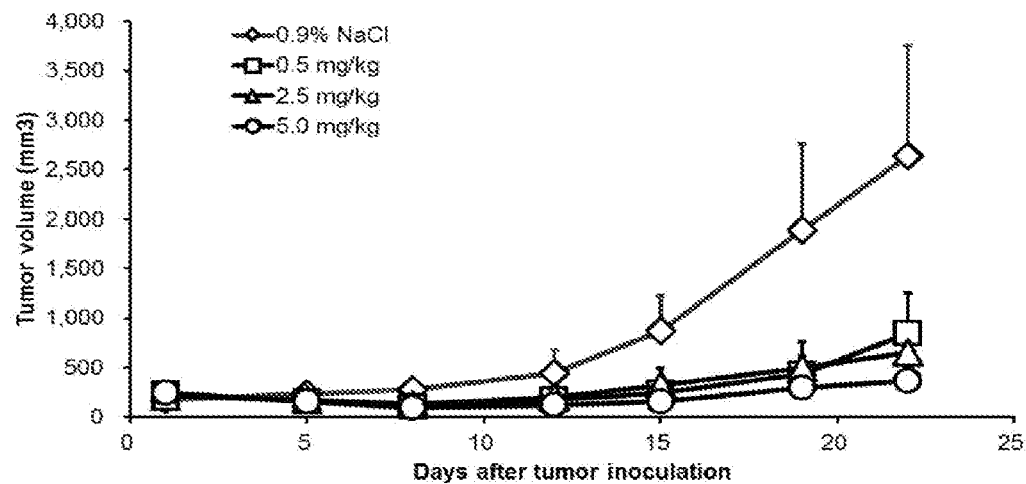
[Figure 6]
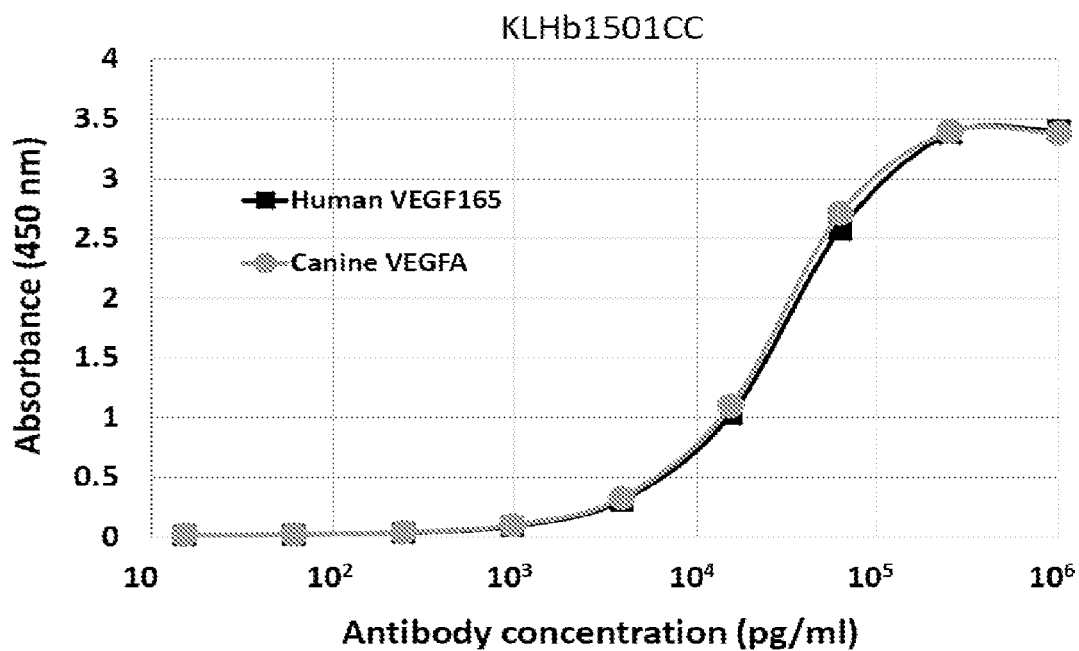

[Figure 7]
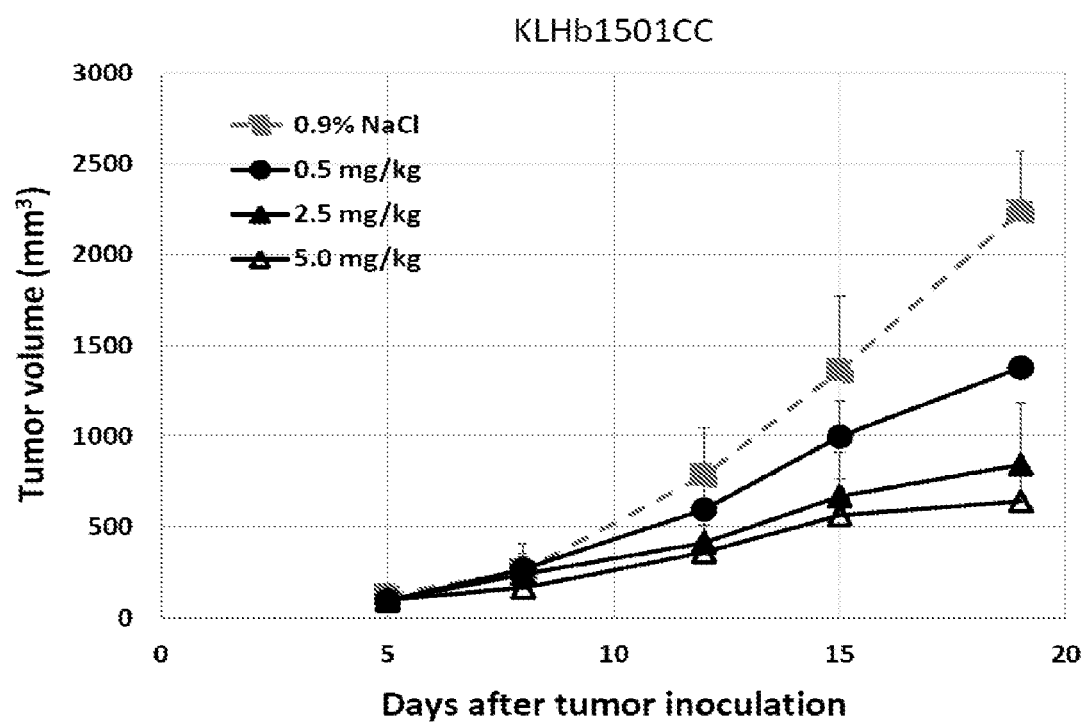

[Figure 8]
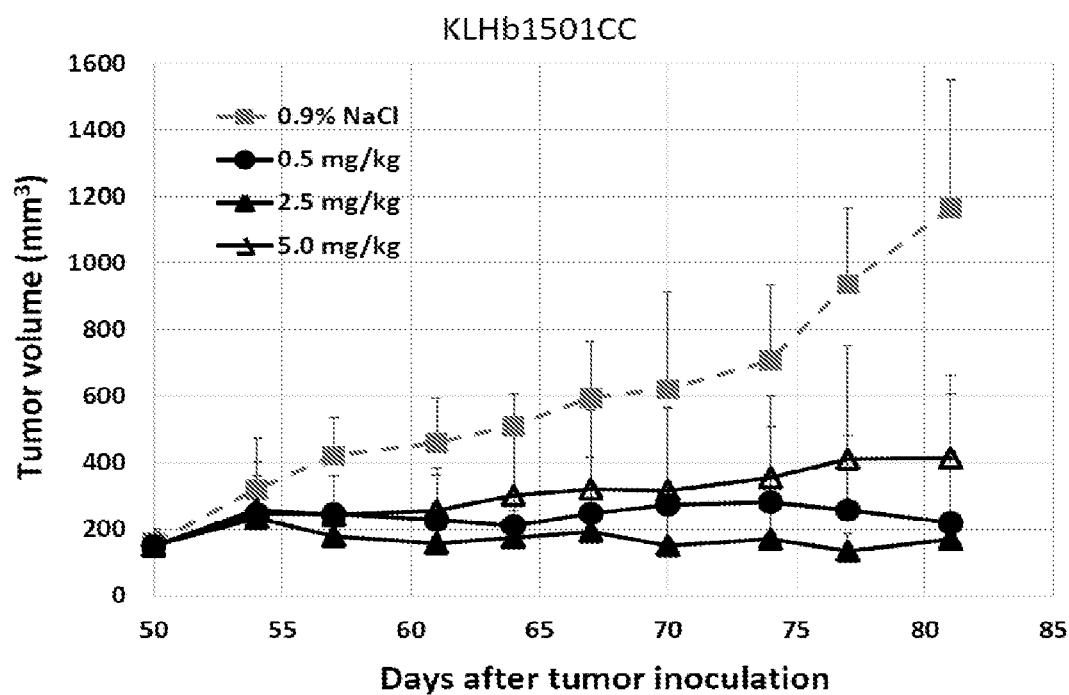

[Figure 9]
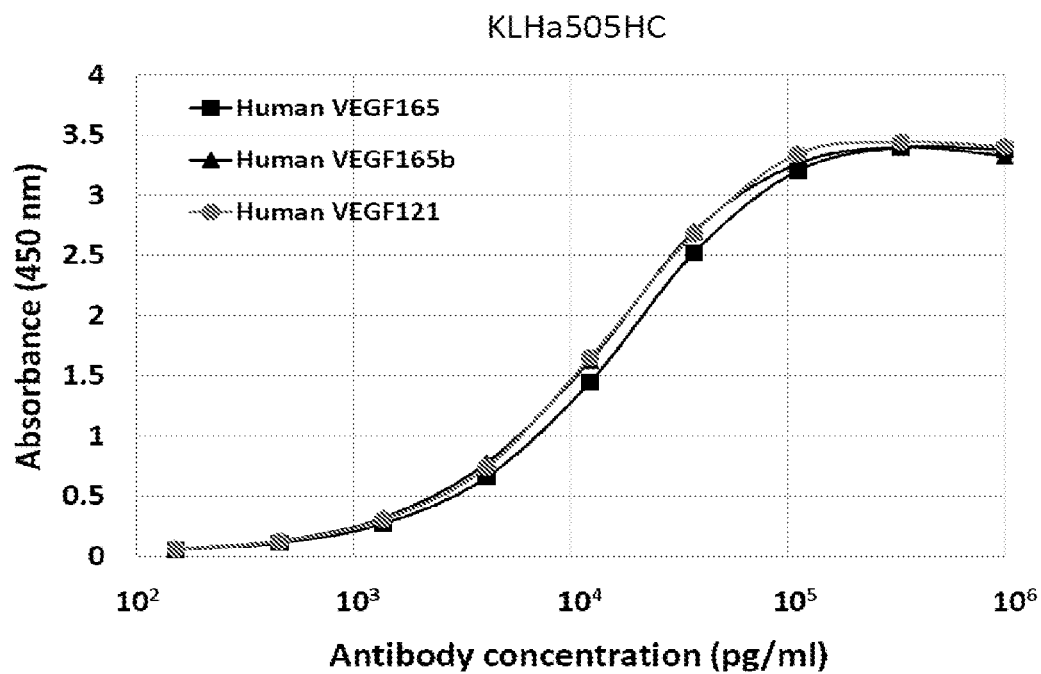

[Figure 10]
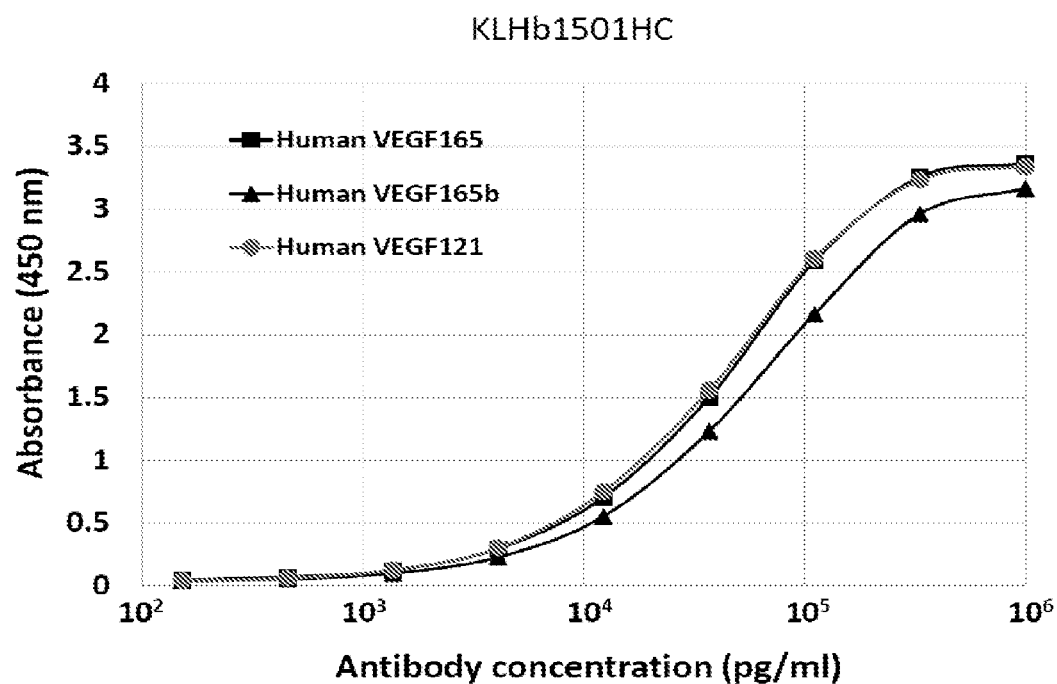

```
                        SEQUENCE LISTING

<160> NUMBER OF SEQ ID NOS: 54

<210> SEQ ID NO 1
<211> LENGTH: 3487
<212> TYPE: DNA
<213> ORGANISM: Mus musculus

<400> SEQUENCE: 1
cggcggcagc ggagctctgt cgcgagacgc agcgacaagg cagactattc agcggactca      60
ccagcccggg agtctgtgct ctgggatttg atattcaaac ctcttaattt ttttttctta     120
aactgtattg ttttacgctt taatttattt ttgcttccta ttccctctt aaatcgtgcc      180 aacggtttga ggaggttggt tcttcactcc ctcaaatcac ttcggattgt ggaaatcagc     240
agacgaaaga ggtatcaaga gctccagaga gaagtcaagg aagagagaga gagaccggtc     300
agagagagcg cgctggcgag cgaacagaga gagggacagg ggcaaagtga ctgacctgct     360 tttggggtg accgccagag cgcggcgtga gccctccccc ttgggatctt gcatcggacc     420
agtcgcgctg acggacagac agacagacac cgcccccagc cccagcgccc acctcctcgc     480
cggcgggctg ccgacggtgg acgcggcggc gagccgcgag gaaccgaagc ccgcgcccgg     540
aggcggggtg gaggggtcg gggctcgcgg gattgcacgg aaacttttcg tccaacttct      600
gggctcttct cgctccgtag tagccgtggt ctgcgccgca ggagacaaac cgatcggagc     660
tgggagaagt gctagctcgg gcctggagaa gccggggccc gagaagagag gggaggaaga     720
gaaggaagag gagaggggc cgcagtgggc gctcggctct caggagccga gctcatggac      780
gggtgaggcg gccgtgtgcg cagacagtgc tccagccgcg cgcgcgcccc aggccccggc     840
ccgggcctcg gttccagaag ggagaggagc ccgccaaggc gcgcaagaga gcgggctgcc     900
tcgcagtccg agcggagag ggagcgcgag ccgcgccggc cccggacggg cctccgaaac      960
catgaacttt ctgctctctt gggtgcactg gaccctggct ttactgctgt acctccacca    1020
tgccaagtgg tcccaggctg cacccacgac agaaggagag cagaagtccc atgaagtgat    1080
caagttcatg gatgtctacc agcgaagcta ctgccgtccg attgagaccc tggtggacat    1140
cttccaggag taccccgacg agatagagta catcttcaag ccgtcctgtg tgccgctgat    1200
gcgctgtgca ggctgctgta acgatgaagc cctggagtgc gtgcccacgt cagagagcaa    1260
catcaccatg cagatcatgc ggatcaaacc tcaccaaagc cagcacatag agagatgag     1320 cttcctacag cacagcagat gtgaatgcag accaaagaaa gacagaacaa gccagaaaa    1380 aaaatcagtt cgaggaaagg gaaagggtca aaaacgaaag cgcaagaaat cccggtttaa    1440
atcctggagc gttcactgtg agccttgttc agagcggaga aagcatttgt ttgtccaaga    1500
tccgcagacg tgtaaatgtt cctgcaaaaa cacagactcg cgttgcaagg cgaggcagct    1560
tgagttaaac gaacgtactt gcagatgtga caagccaagg cggtgagcca ggctgcagga    1620
aggagcctcc ctcagggttt cgggaaccag acctctcacc ggaaagaccg attaaccatg    1680
tcaccaccac gccatcatcg tcaccgttga cagaacagtc cttaatccag aaagcctgac    1740
atgaaggaag aggagactct tcgaggagca ctttgggtcc ggagggcgag actccggcag    1800
acgcattccc gggcaggtga ccaagcacgg tccctcgtgg gactggattc gccattttct    1860
tatatctgct gctaaatcgc caagcccgga agattagggt tgtttctggg attcctgtag    1920
```

| | | |
|---|---|---|
| acacacccac ccacatacac acatatatat atattatata tataaataaa tatatatgtt | 1980 | |
| ttatatataa aatatatata tattctttttt tttaaattaa ctctgctaat gttattggtg | 2040 | |
| tcttcactgg atatgtttga ctgctgtgga cttgtgttgg gaggaggatg tcctcactcg | 2100 | |
| gatgccgaca cgggagacaa tgggatgaaa ggcttcagtg tggtctgaga gaggccgaag | 2160 | |
| tccttttgcc tgccggggag caagcaaggc cagggcacgg gggcacattg gctcacttcc | 2220 | |
| agaaacacga caaacccatt cctggccctg agtcaagagg acagagagac agatgatgac | 2280 | |
| agagaaagag ataaagatgc cggttccaac cagaagtttg gggagcctca ggacatggca | 2340 | |
| tgctttgtgg atccccatga tagtctacaa aagcaccccg cccctctggg cactgcctgg | 2400 | |
| aagaatcggg agcctggcca gccttcagct cgctcctcca cttctgaggg gcctaggagg | 2460 | |
| cctcccacag gtgtcccggc aagagaagac acggtggtgg aagaagaggc ctggtaatgg | 2520 | |
| cccctcctcc tgggaccccct tcgtcctctc cttaccccac ctcctgggta cagcccagga | 2580 | |
| ggaccttgtg tgatcagacc attgaaacca ctaattctgt ccccaggaga cttggctgtg | 2640 | |
| tgtgtgagtg gcttacccttt cctcatcttc ccttcccaag gcacagagca atggggcagg | 2700 | |
| acccgcaagc ccctcacgga ggcagagaaa agagaaagtg tttttatatac ggtacttatt | 2760 | |
| taatagccct ttttaattag aaattaaaac agttaatttta attaaagagt agggtttttt | 2820 | |
| tcagtattct tggttaatat ttaatttcaa ctatttatga gatgtatctc tcgctctctc | 2880 | |
| ttatttgtac ttgtgtgtgt gtgtgtgtgt gtgtgtgtgt gtgtgtgtgt gtgtgtatga | 2940 | |
| aatctgtgtt tccaatctct ctctcccaga tcggtgacag tcactagctt gtcctgagaa | 3000 | |
| gatatttaat tttgctaaca ctcagctctg ccctccccttg tccccaccac acattccttt | 3060 | |
| gaaataaggt ttcaatatac atttacatac tatatatata tttggcaact tgtgtttgta | 3120 | |
| tataaatata tatatatata tatatgttta tgtatatatg tgattctgat aaaatagaca | 3180 | |
| ttgctattct gttttttata tgtaaaaaca aaacaagaaa aatagagaat tctacatact | 3240 | |
| aaatctctct ccttttttaa ttttaatatt tgttatcatt tatttattgg tgctactgtt | 3300 | |
| tatccgtaat aattgtgggg gaaaaagata ttaacatcac gtctttgtct ctagagcagt | 3360 | |
| tttccgagat attccgtagt acatatttat ttttaaacag caacaaagaa atacagatat | 3420 | |
| atcttaaaaa aaaaagcatt ttgtattaaa gaattgaatt ctgatctcaa aaaaaaaaaa | 3480 | |
| aaaaaaa | 3487 | |

<210> SEQ ID NO 2
<211> LENGTH: 392
<212> TYPE: PRT
<213> ORGANISM: Mus musculus

<400> SEQUENCE: 2

Met Thr Asp Arg Gln Thr Asp Thr Ala Pro Ser Pro Ser Ala His Leu
1               5                   10                  15

Leu Ala Gly Gly Leu Pro Thr Val Asp Ala Ala Ala Ser Arg Glu Glu
            20                  25                  30

Pro Lys Pro Ala Pro Gly Gly Gly Val Glu Gly Val Gly Ala Arg Gly
        35                  40                  45

Ile Ala Arg Lys Leu Phe Val Gln Leu Leu Gly Ser Ser Arg Ser Val
    50                  55                  60

Val Ala Val Val Cys Ala Ala Gly Asp Lys Pro Ile Gly Ala Gly Arg
65                  70                  75                  80

Ser Ala Ser Ser Gly Leu Glu Lys Pro Gly Pro Glu Lys Arg Gly Glu
                85                  90                  95

Glu Glu Lys Glu Glu Glu Arg Gly Pro Gln Trp Ala Leu Gly Ser Gln
            100                 105                 110

Glu Pro Ser Ser Trp Thr Gly Glu Ala Ala Val Cys Ala Asp Ser Ala
            115                 120                 125

Pro Ala Ala Arg Ala Pro Gln Ala Pro Ala Arg Ala Ser Val Pro Glu
            130                 135                 140

Gly Arg Gly Ala Arg Gln Gly Ala Gln Glu Ser Gly Leu Pro Arg Ser
145                 150                 155                 160

Pro Ser Arg Arg Gly Ser Ala Ser Arg Ala Gly Pro Gly Arg Ala Ser
                165                 170                 175

Glu Thr Met Asn Phe Leu Leu Ser Trp Val His Trp Thr Leu Ala Leu
            180                 185                 190

Leu Leu Tyr Leu His His Ala Lys Trp Ser Gln Ala Ala Pro Thr Thr
            195                 200                 205

Glu Gly Glu Gln Lys Ser His Glu Val Ile Lys Phe Met Asp Val Tyr
            210                 215                 220

Gln Arg Ser Tyr Cys Arg Pro Ile Glu Thr Leu Val Asp Ile Phe Gln
225                 230                 235                 240

Glu Tyr Pro Asp Glu Ile Glu Tyr Ile Phe Lys Pro Ser Cys Val Pro
                245                 250                 255

Leu Met Arg Cys Ala Gly Cys Cys Asn Asp Glu Ala Leu Glu Cys Val
            260                 265                 270

Pro Thr Ser Glu Ser Asn Ile Thr Met Gln Ile Met Arg Ile Lys Pro
            275                 280                 285

His Gln Ser Gln His Ile Gly Glu Met Ser Phe Leu Gln His Ser Arg
            290                 295                 300

Cys Glu Cys Arg Pro Lys Lys Asp Arg Thr Lys Pro Glu Lys Lys Ser
305                 310                 315                 320

Val Arg Gly Lys Gly Lys Gly Gln Lys Arg Lys Arg Lys Lys Ser Arg
                325                 330                 335

Phe Lys Ser Trp Ser Val His Cys Glu Pro Cys Ser Glu Arg Arg Lys
            340                 345                 350

His Leu Phe Val Gln Asp Pro Gln Thr Cys Lys Cys Ser Cys Lys Asn
            355                 360                 365

Thr Asp Ser Arg Cys Lys Ala Arg Gln Leu Glu Leu Asn Glu Arg Thr
            370                 375                 380

Cys Arg Cys Asp Lys Pro Arg Arg
385                 390

<210> SEQ ID NO 3
<211> LENGTH: 3561
<212> TYPE: DNA
<213> ORGANISM: Rattus norvegicus

<400> SEQUENCE: 3
ttggggcagc cgagctgcag cgaggccgcg gcgctggggg cgagctgagc ggcggcagcg    60
gagctctgtc gcgagacgca gcgacaaggc agactattca acggactcat cagccaggga   120
gtctgtgctc tgggatttga tattcaaacc tctttttttt ttcttaaact gtattgtttt   180
acgctttaat ttatttttgc ttcctattcc cctcttaaat cgtgccaacg gtttggagag   240
gttgctcctt cactccctca aattacttcg gattttggaa atcagcagag gaaagaggta   300
gcaggagctc cagagagaag tcaaggaaga gagagagaga gagagaccgg tcagagagcg   360
cgctggcgag cgaacagaga gagggacagg ggcaaagtga ctgacctgct tttgggggtg   420

```
accgccagag cgcggcgtga gccctccccc ttgggatctt tcatcggacc agtcgcgctg    480
acggacagac agacagacac cgcccccagc cccagcgccc acctcctcgc cggcgggcag    540
ccgacggtgg acgcggcggc gagccgcgag caggagccga agcccgcgcc cggaggcggg    600 gtggagggggg tcgggctcg cgggattgca cggaaacttt tcgtccaact tctgggctct    660
tctctctccg gagtagccgt ggtctgcgcc gcaggaggca aaccgatcgg agctgggaga    720
agtgctagct cgggcctgga gaagccgggg cccgagaaga gagggagaa agagaaggaa     780 gaggagaggg ggccgcagtg ggcgctcggc tctcgggagc cgggctcatg acgggtgag     840 gcggcggtgt gcgcagacag tgctccagcc gcgcgcgcgc cccaggcccc ggcccgggcc    900
tcggttccag aagggagagg agcccgccaa ggcgcgcaag agagcgggct gcctcgcagt    960
ccgagccgga gagggagcgc gagccgcgcc ggccccggac gggcctctga aaccatgaac   1020
tttctgctct cttgggtgca ctggaccctg gctttactgc tgtacctcca ccatgccaag   1080
tggtcccagg ctgcacccac gacagaaggg gagcagaaag cccatgaagt ggtgaagttc   1140
atggacgtct accagcgcag ctattgccgt ccaattgaga cccctggtgga catcttccag   1200 gagtaccccg atgagataga gtatatcttc aagccgtcct gtgtgcccct aatgcggtgt   1260
gcgggctgct gcaatgatga agccctggag tgcgtgccca cgtcggagag caacgtcact   1320
atgcagatca tgcggatcaa acctcaccaa agccagcaca taggagagat gagcttcctg   1380
cagcatagca gatgtgaatg cagaccaaag aaagatagaa caaagccaga aaaaaaatca   1440
gttcgaggaa agggaaaggg tcaaaaacga aagcgcaaga aatcccggtt taaatcctgg   1500
agcgttcact gtgagccttg ttcagagcgg agaaagcatt tgtttgtcca agatccgcag   1560
acgtgtaaat gttcctgcaa aaacacagac tcgcgttgca aggcgaggca gcttgagtta   1620
aacgaacgta cttgcagatg tgacaagcca aggcggtgag ccaggctgca ggaaggagcc   1680
tccctcaggg tttcgggaac tagacctctc accggaaaga ccgattaacc atgtcaccac   1740
cacaccacca tcgtcaccgt cgacagaaca gtccttaatc cagaaagcct gacatgaagg   1800
gagaggagac tcttcgagga gcactttggg tccggagggc gagactccgg cagacgcatt   1860
cccgggcagg tgaccaagca cggtggtccc tcgtggaact ggattcgcca ttttcttata   1920
tttgctgcta aatcgccaag cccggaagat tagggagttt tgtttctggg attcctgtag   1980
acacacccac ccacatacac acacatatat atatatatat tatatatata aataaaatata   2040 tatgttttat atataaaata tatatatatt ctttttttt ttaaattaac tctgctaatg    2100
ttattggtgt cttcactgga tatgtttgac tgctgtggac ttgagttggg aggaggatgt   2160
cctcacttgg atcccgacag ggaagacaat gggatgaaag actccggtgt ggtctttcgt   2220
ccttcttaga gaggccgaag tctgtttgcc tgccagggag cacgcaaggc cagggcacgg   2280
gggcacgttg gctcacttcc agaaacacga caaacccatc cctggccctg agtcaagagg   2340
acagagagac agatgacaga taaagagata aagattctgg ttccgaccag acgttttggg   2400
ggagcctcag gacatggcac tattgtggat ccccactaga ttctgcaaga gcaccctgcc   2460
cctctgggca ctgcctggaa gaatcaggag cctggccatc aagctctctc ctccacttct   2520
gaggagccta ggaggcctcc cacaggggtc ctggcaaaga gaagacacag tggtggaaga   2580
agaggcctgg taatggctcc tcctcctcct cctgggaacc cctcgtcctc tccctacccc   2640
acttcctggg tatagctcag gaggaccttg tgtgatcaga ccattgaaac cactaattct   2700
gtccccagga gacttggctg tgtgtgtgag tggcttaccc ttccccattt tcccttccca   2760
```

-continued

```
aggtacagag caatggggca ggacccgcaa gcccctcatg gaggcagaga aaagagaaag    2820
tgttttatat acggtactta tttaatagcc cttttaatt agaaattaaa acagttaatt     2880
taattaaaga gtagggtttt tttcagtatt cttggttaat atttaatttc aactatttat   2940
gaggatgcat ctcttgctct ttcttatttg tactgttttt ttttgttttg ttttctgtg    3000 tgtgtgtgtg tatgaaatct gtgtttccaa tctctctctc ccagatcggt gacagtcact   3060
agcttgtcct gagaagatat ttaattttgc taacactcag ctctgccctc ccctgtcccc   3120
accacacatt cctttgaaat aaggtttcaa tatacattta catactatat atatatttgg   3180
caacttgtgt ttgtatataa atatatatat atatatatgt ttatgtatat atgtgattct   3240
gataaaatag acattgctat tctgtttttt atatgtaaaa acaaaacgag aaaaaataga   3300
gaattctaca tactaaatct ctctcctttt ttaattttaa tatttgttat catttattta   3360
ttggtgctac tgtttatccg taataattgt gggggaaaag atattaacat cacgtctttg   3420
tctctagagc agttttccga gatattccgt agtacatatt tattttaaa cagcaacaaa    3480 gaaatacaga tatatcttaa gaaaaaaaaa gcattttgta ttaagaatt gaattctgat    3540 ctcaaaaaaa aaaaaaaaaa a                                            3561
```

<210> SEQ ID NO 4
<211> LENGTH: 393
<212> TYPE: PRT
<213> ORGANISM: Rattus norvegicus

<400> SEQUENCE: 4

```
Met Thr Asp Arg Gln Thr Asp Thr Ala Pro Ser Pro Ser Ala His Leu
1               5                   10                  15

Leu Ala Gly Gly Gln Pro Thr Val Asp Ala Ala Ala Ser Arg Glu Gln
            20                  25                  30

Glu Pro Lys Pro Ala Pro Gly Gly Val Glu Gly Val Gly Ala Arg
        35                  40                  45

Gly Ile Ala Arg Lys Leu Phe Val Gln Leu Leu Gly Ser Ser Leu Ser
    50                  55                  60

Gly Val Ala Val Val Cys Ala Ala Gly Gly Lys Pro Ile Gly Ala Gly
65                  70                  75                  80

Arg Ser Ala Ser Ser Gly Leu Glu Lys Pro Gly Pro Glu Lys Arg Gly
                85                  90                  95

Glu Lys Glu Lys Glu Glu Arg Gly Pro Gln Trp Ala Leu Gly Ser
            100                 105                 110

Arg Glu Pro Gly Ser Trp Thr Gly Glu Ala Ala Val Cys Ala Asp Ser
        115                 120                 125

Ala Pro Ala Ala Arg Ala Pro Gln Ala Pro Ala Arg Ala Ser Val Pro
    130                 135                 140

Glu Gly Arg Gly Ala Arg Gln Gly Ala Gln Glu Ser Gly Leu Pro Arg
145                 150                 155                 160

Ser Pro Ser Arg Arg Gly Ser Ala Ser Arg Ala Gly Pro Gly Arg Ala
                165                 170                 175

Ser Glu Thr Met Asn Phe Leu Leu Ser Trp Val His Trp Thr Leu Ala
            180                 185                 190

Leu Leu Leu Tyr Leu His His Ala Lys Trp Ser Gln Ala Ala Pro Thr
        195                 200                 205

Thr Glu Gly Glu Gln Lys Ala His Glu Val Val Lys Phe Met Asp Val
    210                 215                 220

Tyr Gln Arg Ser Tyr Cys Arg Pro Ile Glu Thr Leu Val Asp Ile Phe
```

```
                    225                 230                 235                 240
            Gln Glu Tyr Pro Asp Glu Ile Glu Tyr Ile Phe Lys Pro Ser Cys Val
                        245                 250                 255
            Pro Leu Met Arg Cys Ala Gly Cys Cys Asn Asp Glu Ala Leu Glu Cys
                        260                 265                 270
            Val Pro Thr Ser Glu Ser Asn Val Thr Met Gln Ile Met Arg Ile Lys
                        275                 280                 285
            Pro His Gln Ser Gln His Ile Gly Glu Met Ser Phe Leu Gln His Ser
                        290                 295                 300
            Arg Cys Glu Cys Arg Pro Lys Lys Asp Arg Thr Lys Pro Glu Lys Lys
            305                 310                 315                 320
            Ser Val Arg Gly Lys Gly Lys Gly Gln Lys Arg Lys Arg Lys Lys Ser
                        325                 330                 335
            Arg Phe Lys Ser Trp Ser Val His Cys Glu Pro Cys Ser Glu Arg Arg
                        340                 345                 350
            Lys His Leu Phe Val Gln Asp Pro Gln Thr Cys Lys Cys Ser Cys Lys
                        355                 360                 365
            Asn Thr Asp Ser Arg Cys Lys Ala Arg Gln Leu Glu Leu Asn Glu Arg
                        370                 375                 380
            Thr Cys Arg Cys Asp Lys Pro Arg Arg
            385                 390

<210> SEQ ID NO 5
<211> LENGTH: 2828
<212> TYPE: DNA
<213> ORGANISM: Canis lupus familiaris
<220> FEATURE:
<221> NAME/KEY: CDS
<222> LOCATION: (278)..(922)

<400> SEQUENCE: 5
ggaggagggg gaggaggaag aagagaagga agaggagagg gggccgcggt ggcgactcgg        60
cgttcgggag ccgggctcat ggacgggtga ggcggctgtg tgcgcagaca gagctccagc       120
cgcgcgcgcg ccccaggccc cggccccggc cccggcccgg gcctcggctc cggaggaaag       180
aggagcccgc ctaggcgccg aggagagcgg ccgccccgc agcccgagcg ggagagggag        240
cgcgagccgc gccggccccg gccgggcctc cgaaacc atg aac ttt ctg ctc tcc       295
                                         Met Asn Phe Leu Leu Ser
                                           1               5 tgg gtg cat tgg agc ctt gcc ttg ctg ctc tac ctc cac cat gcc aag       343
Trp Val His Trp Ser Leu Ala Leu Leu Leu Tyr Leu His His Ala Lys
         10                  15                  20 tgg tcc cag gct gcg cct atg gca gga gga gag cac aaa ccc cac gaa       391
Trp Ser Gln Ala Ala Pro Met Ala Gly Gly Glu His Lys Pro His Glu
     25                  30                  35 gtg gtg aag ttc atg gac gtc tac cag cgc agc tac tgc cgt ccc att       439
Val Val Lys Phe Met Asp Val Tyr Gln Arg Ser Tyr Cys Arg Pro Ile
 40                  45                  50 gag acc ctg gtg gac atc ttc cag gag tac cct gac gag atc gag tac       487
Glu Thr Leu Val Asp Ile Phe Gln Glu Tyr Pro Asp Glu Ile Glu Tyr
 55                  60                  65                  70 atc ttc aag cca tcc tgc gtg ccc ctg atg cgg tgt ggg ggc tgc tgt       535
Ile Phe Lys Pro Ser Cys Val Pro Leu Met Arg Cys Gly Gly Cys Cys
             75                  80                  85 aat gat gag ggc cta gag tgc gtg ccc act gag gag ttc aac atc acc       583
Asn Asp Glu Gly Leu Glu Cys Val Pro Thr Glu Glu Phe Asn Ile Thr
         90                  95                 100
```

-continued

| | |
|---|---|
| atg cag att atg cgg atc aaa cct cat caa ggc cag cac ata ggg gag<br>Met Gln Ile Met Arg Ile Lys Pro His Gln Gly Gln His Ile Gly Glu<br>105                    110                      115 | 631 |
| atg agt ttc ctg cag cat agc aaa tgt gaa tgc aga cca aag aaa gat<br>Met Ser Phe Leu Gln His Ser Lys Cys Glu Cys Arg Pro Lys Lys Asp<br>120                    125                      130 | 679 |
| aga gca agg caa gaa aaa aaa tca att cga gga aag ggg aag ggg caa<br>Arg Ala Arg Gln Glu Lys Lys Ser Ile Arg Gly Lys Gly Lys Gly Gln<br>135                    140                      145                      150 | 727 |
| aaa aga aag cgc aag aaa tcc cgg tat aaa ccc tgg agc gtt ccc tgt<br>Lys Arg Lys Arg Lys Lys Ser Arg Tyr Lys Pro Trp Ser Val Pro Cys<br>                  155                      160                      165 | 775 |
| ggg cct tgc tca gag cgg aga aag cat ttg ttt gta caa gat ccg cag<br>Gly Pro Cys Ser Glu Arg Arg Lys His Leu Phe Val Gln Asp Pro Gln<br>                170                      175                      180 | 823 |
| acg tgt aaa tgt tcc tgc aaa aac aca gac tcg cgt tgc aag gcg agg<br>Thr Cys Lys Cys Ser Cys Lys Asn Thr Asp Ser Arg Cys Lys Ala Arg<br>185                    190                      195 | 871 |
| cag ctt gag tta aac gaa cgt act tgc aga tgt gac aag ccc agg cgg<br>Gln Leu Glu Leu Asn Glu Arg Thr Cys Arg Cys Asp Lys Pro Arg Arg<br>200                    205                      210 | 919 |
| tga gccgggctgg aagaaggagc ctccctcagg gtttcggaa ccagacctct | 972 |
| caccaggaaa gcctgattca gaatgaccgc tacagaaacc acgccgccgc caccaccacc | 1032 |
| acaccaccat caccagaaca atccttaatc cagaaacctg aaatgaagga agaggagact | 1092 |
| ctgcgcagag cactttgggt ccggagggcg caactccggc agaagcattc ccgggcaggt | 1152 |
| gaccaagcac ggtccctctt ggaattggat cgccattgta ttttttcttgc tgctaaatca | 1212 |
| ccgagcccgg aagattagag agttttattt ctgggattcc tgtagacaca cccacccaca | 1272 |
| tacatacttt tatatatata tataaaatat atatataaaa ataaatatat atattttata | 1332 |
| tatacgtaaa atatatatat tctttttttt taaattaaca ttgctaatgt tattggtgtc | 1392 |
| ttcactggat atatttgact gctgtggact taagttggga ggaggctgtc cccacccaga | 1452 |
| tcccaacagg gaagaggatg ggaggggaga ctctggcatg atcttttggt ccctcgtagg | 1512 |
| aaggccaggg tccccttccc tgcccaggaa cgtgcttggc cagggcacgg gggcaaattt | 1572 |
| ggcctgcttt tggggacact gacaaaccca gccctggccc caagcctcta ccccgagtca | 1632 |
| aatggacaga cgacaggtac agggacgagg acactggctc tgactaggag ttcggggagc | 1692 |
| ctcaggacac tgctgtactt tgaggatcct ctccacatgc tgcacggacg ggcatcttgc | 1752 |
| ccccaggggc actgcctgga agattcagga gactgggcag ccttcaccta ctcttcactt | 1812 |
| gctcctgaca agcccagggt gccgccaaca gaggtcttgg cgaaaagaag agagacattg | 1872 |
| gtggaggaag ggccgcctgg tggcagcttg tcctccgagg gaagggcccc ctgccttggc | 1932 |
| catctcccag ctctccttcc ctggtgcagc ccaggagggc ctgacgtcct cagaccattg | 1992 |
| aaaccactag ttctgtcccc ccaggagacc tggctgcgtg tgtgtgagtg gttcaccctc | 2052 |
| ctctgtcccc agacccgacc cttccgcgcg cacagagaga cagggcagga tccacgtgcc | 2112 |
| caccatggag gcagagaaag tgttttatat acgataatta tttaatatcc cttttaatt | 2172 |
| agaaattaaa acagtaatt taattaaaga gtagggtttt tttcagtatt cttggttaat | 2232 |
| atttaatttc aactatttat gagatgtatc tctctattgc tctctcttgc gctcttatat | 2292 |
| gtaccggtct ttgtgtttaa gattcatgtt ccaatctctc tctccctga tcggtgacag | 2352 |
| tcactagctt gtcctgagca gatatttaat tttgctaaca ctcagctctg ccctccctt | 2412 |
| gcccccggct ccccaccaca cattcctttg aaataaggtt tcaatataca tctacagact | 2472 |

| atatatatat | ttggcaactt | gcgtttgtgt | gtatatatat | atatatatat | atatatatat | 2532 |
| atgtttatgt | atatatgtga | ttctgataaa | atagacattg | ctattctgtt | ttttatatgt | 2592 |
| aaaaacaaaa | caagaaaaaa | tagagaattc | tacatactaa | atctctctcc | ttttttaatt | 2652 |
| ttaatatttg | ttatcattta | tttattggtg | ctactgttta | tccgtaataa | ttgtgggga | 2712 |
| aaaagatatt | aacatcacat | ctttgtctct | agtacagttt | ttcgagatat | tccgtagtac | 2772 |
| atatttattt | ttaaacaaca | acaaagaaat | acagatatat | cttaaaaaaa | aaaaaa | 2828 |

<210> SEQ ID NO 6
<211> LENGTH: 214
<212> TYPE: PRT
<213> ORGANISM: Canis lupus familiaris

<400> SEQUENCE: 6

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Gly Gly
            20                  25                  30

Glu His Lys Pro His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Glu Glu Phe Asn Ile Thr Met Gln Ile Met Arg Ile Lys Pro His Gln
            100                 105                 110

Gly Gln His Ile Gly Glu Met Ser Phe Leu Gln His Ser Lys Cys Glu
        115                 120                 125

Cys Arg Pro Lys Lys Asp Arg Ala Arg Gln Glu Lys Lys Ser Ile Arg
    130                 135                 140

Gly Lys Gly Lys Gly Gln Lys Arg Lys Arg Lys Lys Ser Arg Tyr Lys
145                 150                 155                 160

Pro Trp Ser Val Pro Cys Gly Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
    210

<210> SEQ ID NO 7
<211> LENGTH: 3677
<212> TYPE: DNA
<213> ORGANISM: Homo sapiens

<400> SEQUENCE: 7

| tcgcggaggc | ttggggcagc | cgggtagctc | ggaggtcgtg | gcgctggggg | ctagcaccag | 60 |
| cgctctgtcg | ggaggcgcag | cggttaggtg | gaccggtcag | cggactcacc | ggccagggcg | 120 |
| ctcggtgctg | gaatttgata | ttcattgatc | cgggttttat | ccctcttctt | ttttcttaaa | 180 |
| catttttttt | taaaactgta | ttgtttctcg | ttttaattta | ttttgcttg | ccattcccca | 240 |

```
cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggctc gcggcgtcgc actgaaactt    660
ttcgtccaac ttctgggctg ttctcgcttc ggaggagccg tggtccgcgc ggggaagcc    720 gagccgagcg gagccgcgag aagtgctagc tcggccgggg aggagccgca gccggaggag    780
ggggaggagg aagaagagaa ggaagaggag aggggggccgc agtggcgact cggcgctcgg    840
aagccgggct catggacggg tgaggcggcg gtgtgcgcag acagtgctcc agccgcgcgc    900 gctcccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catccaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtgtacgttg gtgcccgctg ctgtctaatg    1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca tttatttttt cttgctgcta aatcaccgag cccggaagat    2040
tagagagttt tatttctggg attcctgtag acacacccac ccacatacat acatttatat    2100
atatatatat tatatatata taaaaataaa tatctctatt ttatatatat aaaatatata    2160
tattcttttt ttaaattaac agtgctaatg ttattggtgt cttcactgga tgtatttgac    2220
tgctgtggac ttgagttggg aggggaatgt tcccactcag atcctgacag ggaagaggag    2280
gagatgagag actctggcat gatctttttt ttgtcccact tggtggggcc agggtcctct    2340
cccctgccca ggaatgtgca aggccagggc atggggcaa atatgaccca gttttgggaa    2400
caccgacaaa cccagccctg gcgctgagcc tctctacccc aggtcagacg gacagaaaga    2460
cagatcacag gtacagggat gaggacaccg gctctgacca ggagtttggg gagcttcagg    2520
acattgctgt gctttgggga ttccctccac atgctgcacg cgcatctcgc ccccagggc    2580 actgcctgga agattcagga gcctgggcgg ccttcgctta ctctcacctg cttctgagtt    2640
```

-continued

```
gcccaggaga ccactggcag atgtcccggc gaagagaaga gacacattgt tggaagaagc    2700
agcccatgac agctccccct cctgggactc gccctcatcc tcttcctgct ccccttcctg    2760
gggtgcagcc taaaaggacc tatgtcctca caccattgaa accactagtt ctgtccccc    2820 aggagacctg gttgtgtgtg tgtgagtggt tgaccttcct ccatccctg gtccttccct     2880 tcccttcccg aggcacagag agacagggca ggatccacgt gcccattgtg gaggcagaga    2940
aaagagaaag tgttttatat acggtactta tttaatatcc ctttttaatt agaaattaaa    3000
acagttaatt taattaaaga gtagggtttt ttttcagtat tcttggttaa tatttaattt    3060
caactattta tgagatgtat cttttgctct ctcttgctct cttatttgta ccggtttttg    3120
tatataaaat tcatgtttcc aatctctctc tccctgatcg gtgacagtca ctagcttatc    3180
ttgaacagat atttaatttt gctaacactc agctctgccc tccccgatcc cctggctccc    3240
cagcacacat tcctttgaaa taaggtttca atatacatct acatactata tatatatttg    3300
gcaacttgta tttgtgtgta tatatatata tatgtgttta tgtatatatg tgattctgat    3360
aaaatagaca ttgctattct gttttttata tgtaaaaaca aaacaagaaa aaatagagaa    3420
ttctacatac taaatctctc tccttttta attttaatat ttgttatcat ttatttattg    3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
tacagatata tcttaaaaaa aaaaaagcat tttgtattaa agaatttaat tctgatctca    3660
aaaaaaaaaa aaaaaaa                                                    3677
```

<210> SEQ ID NO 8
<211> LENGTH: 412
<212> TYPE: PRT
<213> ORGANISM: Homo sapiens

<400> SEQUENCE: 8

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
```

```
                180             185                 190
Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
        210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Cys Cys Asn Asp Glu Gly Leu
                260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
                340                 345                 350

Leu Met Pro Trp Ser Leu Pro Gly Pro His Pro Cys Gly Pro Cys Ser
            355                 360                 365

Glu Arg Arg Lys His Leu Phe Val Gln Asp Pro Gln Thr Cys Lys Cys
        370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 9
<211> LENGTH: 366
<212> TYPE: DNA
<213> ORGANISM: Artificial
<220> FEATURE:
<223> OTHER INFORMATION: Synthetic DNA

<400> SEQUENCE: 9
gccccgatgg cggaaggtgg tggtcaaaac catcacgagg tagtcaaatt tatggacgtt    60
taccagcgct cttattgcca cccaatcgaa acgctggttg atattttcca ggaatatccg   120
gatgaaatcg aatacatttt caaaccgtct tgtgtcccac tgatgcgctg tggtggctgc   180
tgcaatgacg agggcctgga gtgcgttcca accgaagaat ccaatattac gatgcaaatt   240
atgcgtatta aaccgcacca aggccaacac atcggtgaaa tgtctttcct gcagcacaac   300
aaatgtgaat gtcgcccgaa gaaagaccgt gcacgccagg aaaagtgtga caagccgcgt   360
cgttaa                                                              366

<210> SEQ ID NO 10
<211> LENGTH: 120
<212> TYPE: PRT
<213> ORGANISM: Artificial
<220> FEATURE:
<223> OTHER INFORMATION: Synthetic peptide

<400> SEQUENCE: 10

Ala Pro Met Ala Glu Gly Gly Gly Gln Asn His His Glu Val Val Lys
```

```
1               5                  10                  15
Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
                35                  40                  45

Pro Ser Cys Val Pro Leu Met Arg Cys Gly Gly Cys Cys Asn Asp Glu
            50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                    85                  90                  95

Leu Gln His Asn Lys Cys Glu Cys Arg Pro Lys Lys Asp Arg Ala Arg
                100                 105                 110

Gln Glu Lys Cys Asp Lys Pro Arg
            115                 120
```

<210> SEQ ID NO 11
<211> LENGTH: 576
<212> TYPE: DNA
<213> ORGANISM: Artificial
<220> FEATURE:
<223> OTHER INFORMATION: Synthetic DNA

<400> SEQUENCE: 11

```
atgaactttc tgctgtcttg ggtgcattgg agccttgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca gccatcctg tgtgcccctg      240
atgcgatgcg ggggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga agatagagc aagacaagaa      420
aatccctgtg gccttgctc agagcggaga aagcatttgt ttgtacaaga tccgcagacg     480
tgtaaatgtt cctgcaaaaa cacagactcg cgttgcaagg cgaggcagct tgagttaaac     540
gaacgtactt gcagatgtga caagccgagg cggtga                               576
```

<210> SEQ ID NO 12
<211> LENGTH: 191
<212> TYPE: PRT
<213> ORGANISM: Artificial
<220> FEATURE:
<223> OTHER INFORMATION: Synthetic peptide

<400> SEQUENCE: 12

```
Met Asn Phe Leu Leu Ser Trp Val His Trp Ser Leu Ala Leu Leu Leu
1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
```

```
                85                  90                  95
Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
            165                 170                 175

Leu Glu Leu Asn Glu Arg Thr Cys Arg Cys Asp Lys Pro Arg Arg
            180                 185                 190

<210> SEQ ID NO 13
<211> LENGTH: 24
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(24)

<400> SEQUENCE: 13 ggg tat acc ttc aca aac tat gga                                      24
Gly Tyr Thr Phe Thr Asn Tyr Gly
1               5

<210> SEQ ID NO 14
<211> LENGTH: 8
<212> TYPE: PRT
<213> ORGANISM: Artificial
<220> FEATURE:
<223> OTHER INFORMATION: Synthetic Construct

<400> SEQUENCE: 14

Gly Tyr Thr Phe Thr Asn Tyr Gly
1               5

<210> SEQ ID NO 15
<211> LENGTH: 24
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(24)

<400> SEQUENCE: 15 ata aac acc tac act gga gag cca                                      24
Ile Asn Thr Tyr Thr Gly Glu Pro
1               5

<210> SEQ ID NO 16
<211> LENGTH: 8
<212> TYPE: PRT
<213> ORGANISM: Artificial
<220> FEATURE:
<223> OTHER INFORMATION: Synthetic Construct

<400> SEQUENCE: 16

Ile Asn Thr Tyr Thr Gly Glu Pro
1               5
```

<210> SEQ ID NO 17
<211> LENGTH: 39
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(39)

<400> SEQUENCE: 17 gca aga ttt tcc tac ggt att acc tgg ttc ttc gat gtc       39
Ala Arg Phe Ser Tyr Gly Ile Thr Trp Phe Phe Asp Val
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic Construct

<400> SEQUENCE: 18

Ala Arg Phe Ser Tyr Gly Ile Thr Trp Phe Phe Asp Val
1               5                   10

<210> SEQ ID NO 19
<211> LENGTH: 36
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(36)

<400> SEQUENCE: 19 cag agt ctg ctc aac agt aga acc cga aag aac tac           36
Gln Ser Leu Leu Asn Ser Arg Thr Arg Lys Asn Tyr
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic Construct

<400> SEQUENCE: 20

Gln Ser Leu Leu Asn Ser Arg Thr Arg Lys Asn Tyr
1               5                   10

<210> SEQ ID NO 21
<211> LENGTH: 24
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(24)

<400> SEQUENCE: 21 aag caa tct tat aat ctg tac acg                           24
Lys Gln Ser Tyr Asn Leu Tyr Thr
1               5

```
<210> SEQ ID NO 22
<211> LENGTH: 8
<212> TYPE: PRT
<213> ORGANISM: Artificial
<220> FEATURE:
<223> OTHER INFORMATION: Synthetic Construct

<400> SEQUENCE: 22

Lys Gln Ser Tyr Asn Leu Tyr Thr
1               5

<210> SEQ ID NO 23
<211> LENGTH: 27
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(27)

<400> SEQUENCE: 23 ggc tac tca atc acc agt gat tat gcc                          27
Gly Tyr Ser Ile Thr Ser Asp Tyr Ala
1               5

<210> SEQ ID NO 24
<211> LENGTH: 9
<212> TYPE: PRT
<213> ORGANISM: Artificial
<220> FEATURE:
<223> OTHER INFORMATION: Synthetic Construct

<400> SEQUENCE: 24

Gly Tyr Ser Ile Thr Ser Asp Tyr Ala
1               5

<210> SEQ ID NO 25
<211> LENGTH: 21
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(21)

<400> SEQUENCE: 25 ata agc tac agt ggt agc act                                  21
Ile Ser Tyr Ser Gly Ser Thr
1               5

<210> SEQ ID NO 26
<211> LENGTH: 7
<212> TYPE: PRT
<213> ORGANISM: Artificial
<220> FEATURE:
<223> OTHER INFORMATION: Synthetic Construct

<400> SEQUENCE: 26

Ile Ser Tyr Ser Gly Ser Thr
1               5

<210> SEQ ID NO 27
<211> LENGTH: 45
<212> TYPE: DNA
<213> ORGANISM: Artificial
<220> FEATURE:
<223> OTHER INFORMATION: Synthetic DNA
```

```
<220> FEATURE:
<221> NAME/KEY: CDS
<222> LOCATION: (1)..(45)

<400> SEQUENCE: 27 gca aga ggg ggg gat tac tac ggt agt cgc ccc tgg ttt gct tac        45
Ala Arg Gly Gly Asp Tyr Tyr Gly Ser Arg Pro Trp Phe Ala Tyr
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic Construct

<400> SEQUENCE: 28

Ala Arg Gly Gly Asp Tyr Tyr Gly Ser Arg Pro Trp Phe Ala Tyr
1               5                   10                  15

<210> SEQ ID NO 29
<211> LENGTH: 27
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(27)

<400> SEQUENCE: 29 act ggg gct gtt aca att agt aac tac                                27
Thr Gly Ala Val Thr Ile Ser Asn Tyr
1               5

<210> SEQ ID NO 30
<211> LENGTH: 9
<212> TYPE: PRT
<213> ORGANISM: Artificial
<220> FEATURE:
<223> OTHER INFORMATION: Synthetic Construct

<400> SEQUENCE: 30

Thr Gly Ala Val Thr Ile Ser Asn Tyr
1               5

<210> SEQ ID NO 31
<211> LENGTH: 27
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(27)

<400> SEQUENCE: 31 gct ctc tgg tac agc aac cat ttg gtg                                27
Ala Leu Trp Tyr Ser Asn His Leu Val
1               5

<210> SEQ ID NO 32
<211> LENGTH: 9
<212> TYPE: PRT
<213> ORGANISM: Artificial
<220> FEATURE:
<223> OTHER INFORMATION: Synthetic Construct

<400> SEQUENCE: 32
```

Ala Leu Trp Tyr Ser Asn His Leu Val
1               5

<210> SEQ ID NO 33
<211> LENGTH: 360
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(360)

<400> SEQUENCE: 33

```
cag atc cag ttg gtg cag tct gga cct gag ctg aag aag cct gga gag      48
Gln Ile Gln Leu Val Gln Ser Gly Pro Glu Leu Lys Lys Pro Gly Glu
1               5                   10                  15 aca gtc aag atc tcc tgc aag gct tct ggg tat acc ttc aca aac tat      96
Thr Val Lys Ile Ser Cys Lys Ala Ser Gly Tyr Thr Phe Thr Asn Tyr
            20                  25                  30 gga atg aac tgg gtg aag cag gct cca gga aag ggt tta aag tgg atg     144
Gly Met Asn Trp Val Lys Gln Ala Pro Gly Lys Gly Leu Lys Trp Met
        35                  40                  45 ggc tgg ata aac acc tac act gga gag cca aca tat ctt gat gac ttc     192
Gly Trp Ile Asn Thr Tyr Thr Gly Glu Pro Thr Tyr Leu Asp Asp Phe
    50                  55                  60 aag gga cgg ttt gcc ttc tct ttg gaa acc tct gcc agc act gcc tac     240
Lys Gly Arg Phe Ala Phe Ser Leu Glu Thr Ser Ala Ser Thr Ala Tyr
65                  70                  75                  80 ttg cag atc aac aac ctc aaa aat gag gac acg tct aca tat ttc tgt     288
Leu Gln Ile Asn Asn Leu Lys Asn Glu Asp Thr Ser Thr Tyr Phe Cys
                85                  90                  95 gca aga ttt tcc tac ggt att acc tgg ttc ttc gat gtc tgg ggc gca     336
Ala Arg Phe Ser Tyr Gly Ile Thr Trp Phe Phe Asp Val Trp Gly Ala
            100                 105                 110 ggg acc acg gtc acc gtc tcc tca                                      360
Gly Thr Thr Val Thr Val Ser Ser
        115                 120
```

<210> SEQ ID NO 34
<211> LENGTH: 120
<212> TYPE: PRT
<213> ORGANISM: Artificial
<220> FEATURE:
<223> OTHER INFORMATION: Synthetic Construct

<400> SEQUENCE: 34

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Leu Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ser Thr Tyr Phe Cys
                85                  90                  95

Ala Arg Phe Ser Tyr Gly Ile Thr Trp Phe Phe Asp Val Trp Gly Ala
            100                 105                 110

```
Gly Thr Thr Val Thr Val Ser Ser
        115                 120
```

<210> SEQ ID NO 35
<211> LENGTH: 337
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(336)

<400> SEQUENCE: 35

```
gac att gtg atg tca cag tct cca tcc tcc ctg gct gtg tca gca gga      48
Asp Ile Val Met Ser Gln Ser Pro Ser Ser Leu Ala Val Ser Ala Gly
1               5                   10                  15 gag aag gtc act atg agc tgc aaa tcc agt cag agt ctg ctc aac agt      96
Glu Lys Val Thr Met Ser Cys Lys Ser Ser Gln Ser Leu Leu Asn Ser
            20                  25                  30 aga acc cga aag aac tac ttg gct tgg tac cag cag aaa cca ggg cag     144
Arg Thr Arg Lys Asn Tyr Leu Ala Trp Tyr Gln Gln Lys Pro Gly Gln
        35                  40                  45 tct cct aaa ctg ctg atc tac tgg gca tcc act agg gaa tct ggg gtc     192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc     240
Pro Asp Arg Phe Thr Gly Ser Gly Ser Gly Thr Asp Phe Thr Leu Thr
65                  70                  75                  80 atc agc agt gtg cag gct gaa gac ctg gca gtt tat tac tgc aag caa     288
Ile Ser Ser Val Gln Ala Glu Asp Leu Ala Val Tyr Tyr Cys Lys Gln
                85                  90                  95 tct tat aat ctg tac acg ttc gga ggg ggg acc aag ctg gaa ata aaa c   337
Ser Tyr Asn Leu Tyr Thr Phe Gly Gly Gly Thr Lys Leu Glu Ile Lys
            100                 105                 110
```

<210> SEQ ID NO 36
<211> LENGTH: 112
<212> TYPE: PRT
<213> ORGANISM: Artificial
<220> FEATURE:
<223> OTHER INFORMATION: Synthetic Construct

<400> SEQUENCE: 36

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110
```

<210> SEQ ID NO 37
<211> LENGTH: 367

<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(366)

<400> SEQUENCE: 37

```
gat gtg cag ctt cag gag tcg gga cct ggc ctg gtg aaa cct tct cag      48
Asp Val Gln Leu Gln Glu Ser Gly Pro Gly Leu Val Lys Pro Ser Gln
1               5                   10                  15 tct ctg tcc ctc acc tgc act gtc act ggc tac tca atc acc agt gat      96
Ser Leu Ser Leu Thr Cys Thr Val Thr Gly Tyr Ser Ile Thr Ser Asp
            20                  25                  30 tat gcc tgg acc tgg atc cgg cag ttt cca gga gac aaa ctg gag tgg     144
Tyr Ala Trp Thr Trp Ile Arg Gln Phe Pro Gly Asp Lys Leu Glu Trp
        35                  40                  45 atg ggc tac ata agc tac agt ggt agc act cgc tac aac cca tct ctc     192
Met Gly Tyr Ile Ser Tyr Ser Gly Ser Thr Arg Tyr Asn Pro Ser Leu
    50                  55                  60 aaa agt cga atc tct atc act cga gac aca tcc aag aac cag ttc ttc     240
Lys Ser Arg Ile Ser Ile Thr Arg Asp Thr Ser Lys Asn Gln Phe Phe
65                  70                  75                  80 ctg cac ttg aat tct gtg act act gag gac acg gcc aca tat ttc tgt     288
Leu His Leu Asn Ser Val Thr Thr Glu Asp Thr Ala Thr Tyr Phe Cys
                85                  90                  95 gca aga ggg ggg gat tac tac ggt agt cgc ccc tgg ttt gct tac tgg     336
Ala Arg Gly Gly Asp Tyr Tyr Gly Ser Arg Pro Trp Phe Ala Tyr Trp
            100                 105                 110 ggc caa ggg act ctg gtc act gtc tct gca g                           367
Gly Gln Gly Thr Leu Val Thr Val Ser Ala
        115                 120
```

<210> SEQ ID NO 38
<211> LENGTH: 122
<212> TYPE: PRT
<213> ORGANISM: Artificial
<220> FEATURE:
<223> OTHER INFORMATION: Synthetic Construct

<400> SEQUENCE: 38

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Thr Trp Ile Arg Gln Phe Pro Gly Asp Lys Leu Glu Trp
        35                  40                  45

Met Gly Tyr Ile Ser Tyr Ser Gly Ser Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Phe Cys
                85                  90                  95

Ala Arg Gly Gly Asp Tyr Tyr Gly Ser Arg Pro Trp Phe Ala Tyr Trp
            100                 105                 110

Gly Gln Gly Thr Leu Val Thr Val Ser Ala
        115                 120
```

<210> SEQ ID NO 39
<211> LENGTH: 328

<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(327)

<400> SEQUENCE: 39

```
cag gct gtt gtg act cag gaa tct gca ctc acc aca tca cct ggt gaa      48
Gln Ala Val Val Thr Gln Glu Ser Ala Leu Thr Thr Ser Pro Gly Glu
1               5                   10                  15 aca gtc aca ctc act tgt cgc tca agt act ggg gct gtt aca att agt      96
Thr Val Thr Leu Thr Cys Arg Ser Ser Thr Gly Ala Val Thr Ile Ser
            20                  25                  30 aac tac gcc aac tgg gtc caa gaa aaa cca gat cat tta ttc act ggt     144
Asn Tyr Ala Asn Trp Val Gln Glu Lys Pro Asp His Leu Phe Thr Gly
        35                  40                  45 cta ata ggt ggt acc aac aac cga gct cca gat gtt cct gcc aga ttc     192
Leu Ile Gly Gly Thr Asn Asn Arg Ala Pro Asp Val Pro Ala Arg Phe
    50                  55                  60 tca ggc tcc ctg att gga gac aag gct gcc ctc acc atc aca ggg gca     240
Ser Gly Ser Leu Ile Gly Asp Lys Ala Ala Leu Thr Ile Thr Gly Ala
65                  70                  75                  80 cag act gag gat gag gca ata tat ttc tgt gct ctc tgg tac agc aac     288
Gln Thr Glu Asp Glu Ala Ile Tyr Phe Cys Ala Leu Trp Tyr Ser Asn
                85                  90                  95 cat ttg gtg ttc ggt gaa gga acc aaa ctg act gtc cta g               328
His Leu Val Phe Gly Glu Gly Thr Lys Leu Thr Val Leu
                100                 105
```

<210> SEQ ID NO 40
<211> LENGTH: 109
<212> TYPE: PRT
<213> ORGANISM: Artificial
<220> FEATURE:
<223> OTHER INFORMATION: Synthetic Construct

<400> SEQUENCE: 40

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Ile Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Asp Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Glu Gly Thr Lys Leu Thr Val Leu
                100                 105

<210> SEQ ID NO 41
<211> LENGTH: 1004
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(990)

<400> SEQUENCE: 41

```
gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag     720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat     768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac     816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc     864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac     912
Leu Tyr Ser Lys Leu Thr Val Asp Lys Ser Arg Trp Gln Gln Gly Asn
    290                 295                 300
```

| | | | | | | | | | | | | |
|---|---|---|---|---|---|---|---|---|---|---|---|---|
| gtc | ttc | tca | tgc | tcc | gtg | atg | cat | gag | gct | ctg | cac | aac cac tac acg | 960 |
| Val | Phe | Ser | Cys | Ser | Val | Met | His | Glu | Ala | Leu | His | Asn His Tyr Thr |
| 305 | | | | 310 | | | | 315 | | | | 320 |

| | | | | | | | | |
|---|---|---|---|---|---|---|---|---|
| cag | aag | agc | ctc | tcc | ctg | tct | ccg | ggt aaa tgagtcctag ctgg | 1004 |
| Gln | Lys | Ser | Leu | Ser | Leu | Ser | Pro | Gly Lys |
| | | | | 325 | | | | 330 |

<210> SEQ ID NO 42
<211> LENGTH: 330
<212> TYPE: PRT
<213> ORGANISM: Artificial
<220> FEATURE:
<223> OTHER INFORMATION: Synthetic Construct

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys

<210> SEQ ID NO 43
<211> LENGTH: 321
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(318)

<400> SEQUENCE: 43

```
acg gtg gct gca cca tct gtc ttc atc ttc ccg cca tct gat gag cag      48
Thr Val Ala Ala Pro Ser Val Phe Ile Phe Pro Pro Ser Asp Glu Gln
1               5                   10                  15 ttg aaa tct gga act gcc tct gtt gtg tgc ctg ctg aat aac ttc tat      96
Leu Lys Ser Gly Thr Ala Ser Val Val Cys Leu Leu Asn Asn Phe Tyr
            20                  25                  30 ccc aga gag gcc aaa gta cag tgg aag gtg gat aac gcc ctc caa tcg     144
Pro Arg Glu Ala Lys Val Gln Trp Lys Val Asp Asn Ala Leu Gln Ser
        35                  40                  45 ggt aac tcc cag gag agt gtc aca gag cag gac agc aag gac agc acc     192
Gly Asn Ser Gln Glu Ser Val Thr Glu Gln Asp Ser Lys Asp Ser Thr
    50                  55                  60 tac agc ctc agc agc acc ctg acg ctg agc aaa gca gac tac gag aaa     240
Tyr Ser Leu Ser Ser Thr Leu Thr Leu Ser Lys Ala Asp Tyr Glu Lys
65                  70                  75                  80 cac aaa gtc tac gcc tgc gaa gtc acc cat cag ggc ctg agc tcg ccc     288
His Lys Val Tyr Ala Cys Glu Val Thr His Gln Gly Leu Ser Ser Pro
                85                  90                  95 gtc aca aag agc ttc aac agg gga gag tgt tag                         321
Val Thr Lys Ser Phe Asn Arg Gly Glu Cys
            100                 105
```

<210> SEQ ID NO 44
<211> LENGTH: 106
<212> TYPE: PRT
<213> ORGANISM: Artificial
<220> FEATURE:
<223> OTHER INFORMATION: Synthetic Construct

<400> SEQUENCE: 44

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 45
<211> LENGTH: 1008
<212> TYPE: DNA
<213> ORGANISM: Artificial

```
<220> FEATURE:
<223> OTHER INFORMATION: Synthetic DNA
<220> FEATURE:
<221> NAME/KEY: CDS
<222> LOCATION: (1)..(1008)

<400> SEQUENCE: 45 gcc tcc acc acg gcc ccc tcg gtt ttc cca ctg gcc ccc agc tgc ggg        48
Ala Ser Thr Thr Ala Pro Ser Val Phe Pro Leu Ala Pro Ser Cys Gly
1               5                   10                  15 tcc act tcc ggc tcc acg gtg gcc ctg gcc tgc ctg gtg tca ggc tac        96
Ser Thr Ser Gly Ser Thr Val Ala Leu Ala Cys Leu Val Ser Gly Tyr
            20                  25                  30 ttc ccc gag cct gta act gtg tcc tgg aat tcc ggc tcc ttg acc agc       144
Phe Pro Glu Pro Val Thr Val Ser Trp Asn Ser Gly Ser Leu Thr Ser
        35                  40                  45 ggt gtg cac acc ttc ccg tcc gtc ctg cag tcc tca ggg ctc tac tcc       192
Gly Val His Thr Phe Pro Ser Val Leu Gln Ser Ser Gly Leu Tyr Ser
    50                  55                  60 ctc agc agc atg gtg aca gtg ccc tcc agc agg tgg ccc agc gag acc       240
Leu Ser Ser Met Val Thr Val Pro Ser Ser Arg Trp Pro Ser Glu Thr
65                  70                  75                  80 ttc acc tgc aac gtg gcc cac ccg gcc agc aaa act aaa gta gac aag       288
Phe Thr Cys Asn Val Ala His Pro Ala Ser Lys Thr Lys Val Asp Lys
                85                  90                  95 cca gtg ccc aaa aga gaa aat gga aga gtt cct cgc cca cct gat tgt       336
Pro Val Pro Lys Arg Glu Asn Gly Arg Val Pro Arg Pro Pro Asp Cys
            100                 105                 110 ccc aaa tgc cca gcc cct gaa atg ctg gga ggg cct tcg gtc ttc atc       384
Pro Lys Cys Pro Ala Pro Glu Met Leu Gly Gly Pro Ser Val Phe Ile
        115                 120                 125 ttt ccc ccg aaa ccc aag gac acc ctc ttg att gcc cga aca cct gag       432
Phe Pro Pro Lys Pro Lys Asp Thr Leu Leu Ile Ala Arg Thr Pro Glu
    130                 135                 140 gtc aca tgt gtg gtg gtg gat ctg gac cca gaa gac cct gag gtg cag       480
Val Thr Cys Val Val Val Asp Leu Asp Pro Glu Asp Pro Glu Val Gln
145                 150                 155                 160 atc agc tgg ttc gtg gac ggt aag cag atg caa aca gcc aag act cag       528
Ile Ser Trp Phe Val Asp Gly Lys Gln Met Gln Thr Ala Lys Thr Gln
                165                 170                 175 cct cgt gag gag cag ttc aat ggc acc tac cgt gtg gtc agt gtc ctc       576
Pro Arg Glu Glu Gln Phe Asn Gly Thr Tyr Arg Val Val Ser Val Leu
            180                 185                 190 ccc att ggg cac cag gac tgg ctc aag ggg aag cag ttc acg tgc aaa       624
Pro Ile Gly His Gln Asp Trp Leu Lys Gly Lys Gln Phe Thr Cys Lys
        195                 200                 205 gtc aac aac aaa gcc ctc cca tcc ccg atc gag agg acc atc tcc aag       672
Val Asn Asn Lys Ala Leu Pro Ser Pro Ile Glu Arg Thr Ile Ser Lys
    210                 215                 220 gcc aga ggg caa gcc cat cag ccc agt gtg tat gtc ctg ccg cca tcc       720
Ala Arg Gly Gln Ala His Gln Pro Ser Val Tyr Val Leu Pro Pro Ser
225                 230                 235                 240 cgg gag gag ttg agc aag aac aca gtc agc ttg aca tgc ctg atc aaa       768
Arg Glu Glu Leu Ser Lys Asn Thr Val Ser Leu Thr Cys Leu Ile Lys
                245                 250                 255 gac ttc ttc cca cct gac att gat gtg gag tgg cag agc aat gga cag       816
Asp Phe Phe Pro Pro Asp Ile Asp Val Glu Trp Gln Ser Asn Gly Gln
            260                 265                 270 cag gag cct gag agc aag tac cgc acg acc ccg ccc cag ctg gac gag       864
Gln Glu Pro Glu Ser Lys Tyr Arg Thr Thr Pro Pro Gln Leu Asp Glu
        275                 280                 285
```

|  |  |  |  |  |  |  |  |  |  |  |  |  |  |  |  |  |
|---|---|---|---|---|---|---|---|---|---|---|---|---|---|---|---|---|
| gac | ggg | tcc | tac | ttc | ctg | tac | agc | aag | ctc | tct | gtg | gac | aag | agc | cgc | 912 |
| Asp | Gly | Ser | Tyr | Phe | Leu | Tyr | Ser | Lys | Leu | Ser | Val | Asp | Lys | Ser | Arg | |
| 290 | | | | 295 | | | | | 300 | | | | | | | |
| tgg | cag | cgg | gga | gac | acc | ttc | ata | tgt | gcg | gtg | atg | cat | gaa | gct | cta | 960 |
| Trp | Gln | Arg | Gly | Asp | Thr | Phe | Ile | Cys | Ala | Val | Met | His | Glu | Ala | Leu | |
| 305 | | | | 310 | | | | | 315 | | | | | 320 | | |
| cac | aac | cac | tac | aca | cag | gaa | tcc | ctc | tcc | cat | tct | ccg | ggt | aaa | tga | 1008 |
| His | Asn | His | Tyr | Thr | Gln | Glu | Ser | Leu | Ser | His | Ser | Pro | Gly | Lys | | |
| | | | | 325 | | | | | 330 | | | | | 335 | | |

<210> SEQ ID NO 46
<211> LENGTH: 335
<212> TYPE: PRT
<213> ORGANISM: Artificial
<220> FEATURE:
<223> OTHER INFORMATION: Synthetic Construct

<400> SEQUENCE: 46

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
        50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
            325                 330                 335

<210> SEQ ID NO 47
<211> LENGTH: 342
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(342)

<400> SEQUENCE: 47 ctc gag ata aaa aat gat gcc cag cca gcc gtc tat ttg ttc caa cca        48
Leu Glu Ile Lys Asn Asp Ala Gln Pro Ala Val Tyr Leu Phe Gln Pro
1               5                   10                  15 tct cca gac cag tta cac aca gga agt gcc tct gtt gtg tgt ttg ctg        96
Ser Pro Asp Gln Leu His Thr Gly Ser Ala Ser Val Val Cys Leu Leu
            20                  25                  30 aat agc ttc tac ccc aaa gac atc aat gtc aag tgg aaa gtg gat ggt       144
Asn Ser Phe Tyr Pro Lys Asp Ile Asn Val Lys Trp Lys Val Asp Gly
        35                  40                  45 gtc atc caa gac aca ggc atc cag gaa agt gtc aca gag cag gac aag       192
Val Ile Gln Asp Thr Gly Ile Gln Glu Ser Val Thr Glu Gln Asp Lys
    50                  55                  60 gac agt acc tac agc ctc agc agc acc ctg acg atg tcc agt act gag       240
Asp Ser Thr Tyr Ser Leu Ser Ser Thr Leu Thr Met Ser Ser Thr Glu
65                  70                  75                  80 tac cta agt cat gag ttg tac tcc tgt gag atc act cac aag agc ctg       288
Tyr Leu Ser His Glu Leu Tyr Ser Cys Glu Ile Thr His Lys Ser Leu
                85                  90                  95 ccc tcc acc ctc atc aag agc ttc caa agg agc gag tgt cag aga gtg       336
Pro Ser Thr Leu Ile Lys Ser Phe Gln Arg Ser Glu Cys Gln Arg Val
            100                 105                 110 gac tag                                                                342
Asp

<210> SEQ ID NO 48
<211> LENGTH: 113
<212> TYPE: PRT
<213> ORGANISM: Artificial
<220> FEATURE:
<223> OTHER INFORMATION: Synthetic Construct

<400> SEQUENCE: 48

Leu Glu Ile Lys Asn Asp Ala Gln Pro Ala Val Tyr Leu Phe Gln Pro
1               5                   10                  15

Ser Pro Asp Gln Leu His Thr Gly Ser Ala Ser Val Val Cys Leu Leu
            20                  25                  30

Asn Ser Phe Tyr Pro Lys Asp Ile Asn Val Lys Trp Lys Val Asp Gly
        35                  40                  45

Val Ile Gln Asp Thr Gly Ile Gln Glu Ser Val Thr Glu Gln Asp Lys
    50                  55                  60

Asp Ser Thr Tyr Ser Leu Ser Ser Thr Leu Thr Met Ser Ser Thr Glu
65                  70                  75                  80

Tyr Leu Ser His Glu Leu Tyr Ser Cys Glu Ile Thr His Lys Ser Leu
                85                  90                  95

```
                Pro Ser Thr Leu Ile Lys Ser Phe Gln Arg Ser Glu Cys Gln Arg Val
                            100                 105                 110

Asp

<210> SEQ ID NO 49
<211> LENGTH: 318
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(318)

<400> SEQUENCE: 49 cag ccc aag gcc tcc ccc tcg gtc aca ctc ttc ccg ccc tcc tct gag        48
Gln Pro Lys Ala Ser Pro Ser Val Thr Leu Phe Pro Pro Ser Ser Glu
1               5                   10                  15 gag ctc ggc gcc aac aag gcc acc ctg gtg tgc ctc atc agc gac ttc        96
Glu Leu Gly Ala Asn Lys Ala Thr Leu Val Cys Leu Ile Ser Asp Phe
            20                  25                  30 tac ccc agc ggc gtg acg gtg gcc tgg aag gca agc ggc agc ccc gtc       144
Tyr Pro Ser Gly Val Thr Val Ala Trp Lys Ala Ser Gly Ser Pro Val
        35                  40                  45 acc cag ggc gtg gag acc acc aag ccc tcc aag cag agc aac aac aag       192
Thr Gln Gly Val Glu Thr Thr Lys Pro Ser Lys Gln Ser Asn Asn Lys
    50                  55                  60 tac gcg gcc agc agc tac ctg agc ctg acg cct gac aag tgg aaa tct       240
Tyr Ala Ala Ser Ser Tyr Leu Ser Leu Thr Pro Asp Lys Trp Lys Ser
65                  70                  75                  80 cac agc agc ttc agc tgc ctg gtc acg cac gag ggg agc acc gtg gag       288
His Ser Ser Phe Ser Cys Leu Val Thr His Glu Gly Ser Thr Val Glu
                85                  90                  95 aag aag gtg gcc ccc gca gag tgc tct tag                               318
Lys Lys Val Ala Pro Ala Glu Cys Ser
            100                 105

<210> SEQ ID NO 50
<211> LENGTH: 105
<212> TYPE: PRT
<213> ORGANISM: Artificial
<220> FEATURE:
<223> OTHER INFORMATION: Synthetic Construct

<400> SEQUENCE: 50

Gln Pro Lys Ala Ser Pro Ser Val Thr Leu Phe Pro Pro Ser Ser Glu
1               5                   10                  15

Glu Leu Gly Ala Asn Lys Ala Thr Leu Val Cys Leu Ile Ser Asp Phe
            20                  25                  30

Tyr Pro Ser Gly Val Thr Val Ala Trp Lys Ala Ser Gly Ser Pro Val
        35                  40                  45

Thr Gln Gly Val Glu Thr Thr Lys Pro Ser Lys Gln Ser Asn Asn Lys
    50                  55                  60

Tyr Ala Ala Ser Ser Tyr Leu Ser Leu Thr Pro Asp Lys Trp Lys Ser
65                  70                  75                  80

His Ser Ser Phe Ser Cys Leu Val Thr His Glu Gly Ser Thr Val Glu
                85                  90                  95

Lys Lys Val Ala Pro Ala Glu Cys Ser
            100                 105

<210> SEQ ID NO 51
```

```
<211> LENGTH: 114
<212> TYPE: PRT
<213> ORGANISM: Artificial
<220> FEATURE:
<223> OTHER INFORMATION: Synthetic peptide

<400> SEQUENCE: 51

Ala Pro Thr Thr Glu Gly Glu Gln Lys Ser His Glu Val Ile Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Ile Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Asn

<210> SEQ ID NO 52
<211> LENGTH: 114
<212> TYPE: PRT
<213> ORGANISM: Artificial
<220> FEATURE:
<223> OTHER INFORMATION: Synthetic peptide

<400> SEQUENCE: 52

Ala Pro Thr Thr Glu Gly Glu Gln Lys Ala His Glu Val Val Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Val Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Asn

<210> SEQ ID NO 53
<211> LENGTH: 114
<212> TYPE: PRT
<213> ORGANISM: Artificial
<220> FEATURE:
<223> OTHER INFORMATION: Synthetic peptide

<400> SEQUENCE: 53

Ala Pro Met Ala Gly Gly Glu His Lys Pro His Glu Val Val Lys Phe
1               5                   10                  15

Met Asp Val Tyr Gln Arg Ser Tyr Cys Arg Pro Ile Glu Thr Leu Val
            20                  25                  30
```

-continued

```
Asp Ile Phe Gln Glu Tyr Pro Asp Glu Ile Glu Tyr Ile Phe Lys Pro
        35                  40                  45

Ser Cys Val Pro Leu Met Arg Cys Gly Gly Cys Asn Asp Glu Gly
    50                  55                  60

Leu Glu Cys Val Pro Thr Glu Glu Phe Asn Ile Thr Met Gln Ile Met
65                  70                  75                  80

Arg Ile Lys Pro His Gln Gly Gln His Ile Gly Glu Met Ser Phe Leu
                85                  90                  95

Gln His Ser Lys Cys Glu Cys Arg Pro Lys Lys Asp Arg Ala Arg Gln
                100                 105                 110

Glu Asn

<210> SEQ ID NO 54
<211> LENGTH: 115
<212> TYPE: PRT
<213> ORGANISM: Artificial
<220> FEATURE:
<223> OTHER INFORMATION: Synthetic peptide

<400> SEQUENCE: 54

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
                35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Asn
        115
```

HIGH-AFFINITY ANTI-VEGF ANTIBODY KLHA505

This application is a Continuation of co-pending application Ser. No. 16/067,931, filed on Jul. 3, 2018, which is the National Stage Application under 35 U.S.C. § 371 of International Application No. PCT/JP2017/000101, filed on Jan. 5, 2017, which claims the benefit under 35 U.S.C. § 119(a) to Japanese Patent Application No. 2016-001277, filed on Jan. 6, 2016, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "2021_04_13_Sequence_Listing 4456_0243PUS2.txt" created on Apr. 13, 2021 and is 83,692 bytes in size. The sequence listing contained in this .txt file is part of the specification and is hereby incorporated by reference herein in its entirety.

Technical Field

The present invention relates to a high-affinity anti-VEGF antibody.

BACKGROUND ART

Background of the Invention

Vascular endothelial growth factor (VEGF) can induce vasculogenesis (angiogenesis) in vivo, and is a heparin-binding growth factor that is specifically expressed in vascular endothelial cells. Human VEGF protein was purified and identified in 1989. The gene thereof has been cloned and thus the gene sequence has been determined.

VEGF can accelerate vasculogenesis, and all members belonging to the VEGF family bind to receptors (VEGFR) corresponding to respective family molecules existing on cell membrane surfaces and thus to activate cells. As a result of dimerization due to binding of VEGF, the group of these receptors undergoes auto-phosphorylation and is thus activated. VEGFR consists of seven immunoglobulin-like extracellular domains, one transmembrane domain, and one intracellular domain containing a tyrosine kinase region. VEGF-A can bind to VEGF receptor-1 (receptor Flt-1) and VEGF receptor-2 (KDR/Flk-1). Among VEGF receptors, particularly, VEGF receptor-2 mediates almost all known biological functions of VEGF. Regarding VEGF physiological activity and VEGF receptors, Marti et al., (Non Patent Literature 1: Angiogenesis in ischemic disease. Thromb. Haemost. 1999. Supplement 1: 44-52) and Matsumoto et al., (Non Patent Literature 2: VEGF Receptor Signal Transduction. Sci. STKE. 2001. re21) have studied in detail.

In the U.S. and Europe, Avastin® (bevacizumab) that is a recombinant anti-VEGF humanized monoclonal antibody is used for treatment of colorectal cancer, breast cancer, non-small-cell lung cancer, glioma in the central nervous system, and age-related macular degeneration (AMD). The sales of Avastin in 2013 reached US$6,746,000,000, but Avastin does not have high affinity for VEGF (Non Patent Literature 3: Aflibercept as a Treatment for Age-related Macular Degeneration. US Ophthalimic Rev. 2013. 6:58-63). Furthermore, the exclusive production and exclusive form of selling of Avastin force patients who need to use Avastin to pay high medical expenses. Therefore, development of a new anti-VEGF monoclonal antibody is required also from viewpoints of easing the burden of patients and reducing the costs of treatment.

Antibodies having affinity for VEGF higher than that of Avastin have been developed to date, and such antibodies exert tumor suppression superior to Avastin (Patent Literature 1: JP Laid-Open Publication No. 2013-502445).

CITATION LIST

Patent Literature

Patent Literature 1: JP Laid-Open Publication No. 2013-502445

Non Patent Literature

Non Patent Literature 1: Marti et al., Thromb. Haemost. 1999. Supplement 1: 44-52
Non Patent Literature 2: Matsumoto et al., VEGF Receptor Signal Transduction. Sci. STKE. 2001. re21
Non Patent Literature 3: US Ophthalimic Rev., 2013. 6:58-63

SUMMARY OF INVENTION

Technical Problem

The present invention has been achieved under such circumstances. A technical problem to be solved by the present invention is to provide a novel antibody that inhibits the physiological activity of VEGF by binding to a vascular endothelial growth factor (VEGF) with its high affinity for VEGF compared to the prior art to inhibit binding of VEGF to a VEGF receptor.

Solution to Problem

As a result of intensive studies to solve the problem, the present inventors have prepared an antibody that binds to VEGF with high affinity, have discovered that the antibody inhibits the physiological action of VEGF, and thus have completed the present invention.

That is, the present invention is as follows.
(1) A monoclonal antibody against VEGF that binds to a vascular endothelial growth factor (VEGF) with a dissociation constant of $1\times10^{-11}$ mol/L or less.
(2) The monoclonal antibody according to (1) above, wherein the monoclonal antibody inhibits binding of a vascular endothelial growth factor (VEGF) to at least one receptor selected from the group consisting of vascular endothelial growth factor receptor-1 (VEGFR1) and vascular endothelial growth factor receptor-2 (VEGFR2).
(3) A monoclonal antibody that binds to a site to which the monoclonal antibody according to (1) or (2) above binds.
(4) The monoclonal antibody according to any one of (1) to (3) above, wherein the monoclonal antibody is a chimeric antibody or a humanized antibody.
(5) The antibody according to any one of (1) to (4) above, comprising CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18.
(6) The antibody according to any one of (1) to (4) above, comprising CDR-L1 that comprises the amino acid sequence of SEQ ID NO: 20, CDR-L2 that comprises the amino acid sequence of Trp-Ala-Ser, and CDR-L3 that comprises the amino acid sequence of SEQ ID NO: 22.

(7) The antibody according to any one of (1) to (4) above, comprising: CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18; and CDR-L1 that comprises the amino acid sequence of SEQ ID NO: 20, CDR-L2 that comprises the amino acid sequence of Trp-Ala-Ser, and CDR-L3 that comprises the amino acid sequence of SEQ ID NO: 22.

(8) The antibody according to any one of (1) to (4) above, comprising CDR-H1 that comprises the amino acid sequence of SEQ ID NO: 24, CDR-H2 that comprises the amino acid sequence of SEQ ID NO: 26, and CDR-H3 that comprises the amino acid sequence of SEQ ID NO: 28.

(9) The antibody according to any one of (1) to (4) above, comprising CDR-L1 that comprises the amino acid sequence of SEQ ID NO: 30, CDR-L2 that comprises the amino acid sequence of Gly-Thr-Asn, and CDR-L3 that comprises the amino acid sequence of SEQ ID NO: 32.

(10) The antibody according to any one of (1) to (4) above, comprising CDR-H1 that comprises the amino acid sequence of SEQ ID NO: 24, CDR-H2 that comprises the amino acid sequence of SEQ ID NO: 26, and CDR-H3 that comprises the amino acid sequence of SEQ ID NO: 28, and, CDR-L1 that comprises the amino acid sequence of SEQ ID NO: 30, CDR-L2 that comprises the amino acid sequence of Gly-Thr-Asn, and CDR-L3 that comprises the amino acid sequence of SEQ ID NO: 32.

(11) The antibody according to (7) or (10) above, further comprising an amino acid sequence derived from a human IgG1 heavy chain constant region and an amino acid sequence derived from a human IgG1 light chain constant region.

(12) The antibody according to (11) above, wherein the amino acid sequence derived from a human IgG1 heavy chain constant region comprises the amino acid sequence of SEQ ID NO: 42, and the amino acid sequence derived from a human IgG1 light chain constant region comprises the amino acid sequence of SEQ ID NO: 44.

(13) The antibody according to (12) above, comprising:
  a heavy chain that comprises the amino acid sequence of SEQ ID NO: 34 or 38, and the amino acid sequence of SEQ ID NO: 42; and
  a light chain that comprises the amino acid sequence of SEQ ID NO: 36 or 40, and the amino acid sequence of SEQ ID NO: 44.

(14) The antibody according to (7) or (10) above, further comprising an amino acid sequence derived from a canine IgGB heavy chain constant region and an amino acid sequence derived from a canine Ig light chain (κ chain) constant region or a canine Ig light chain (λ chain) constant region.

(15) The antibody according to (14) above, wherein an amino acid sequence derived from a canine IgGB heavy chain constant region comprises the amino acid sequence of SEQ ID NO: 46, an amino acid sequence derived from a canine Ig light chain (κ chain) constant region comprises the amino acid sequence of SEQ ID NO: 48, and an amino acid sequence derived from a canine Ig light chain (λ chain) constant region comprises the amino acid sequence of SEQ ID NO: 50.

(16) The antibody according to (15) above, comprising:
  a heavy chain that comprises the amino acid sequence of SEQ ID NO: 34 or 38 and the amino acid sequence of SEQ ID NO: 46; and
  a light chain that comprises the amino acid sequence of SEQ ID NO: 36 or 40 and the amino acid sequence of SEQ ID NO: 48 or 50.

(17) A fragment of the monoclonal antibody according to any one of (1) to (16) above.

(18) The fragment according to (17) above, wherein the fragment is an antigen-binding fragment.

(19) The fragment according to (18) above, wherein the antigen-binding fragment is a single-chain antibody or a double-chain antibody.

(20) A hybridoma that produces the monoclonal antibody according to any one of (1) to (3) above.

(21) A pharmaceutical composition comprising the monoclonal antibody or the fragment thereof according to any one of (1) to (19) above.

(22) The pharmaceutical composition according to (21) above, for use in treatment or prevention of a VEGF-mediated disease.

(23) The pharmaceutical composition according to (22) above, wherein the VEGF-mediated disease is a cancer or a VEGF-mediated eye disease.

(24) The pharmaceutical composition according to (23) above, wherein the treatment or prevention of the cancer or the VEGF-mediated eye disease is by inhibiting angiogenesis or vascular hyperpermeability.

(25) The pharmaceutical composition according to (24) above, wherein the angiogenesis is pathological angiogenesis.

(26) The pharmaceutical composition according to (23) or (24) above, wherein the cancer is solid cancer or hematologic neoplasm.

(27) The pharmaceutical composition according to (23) or (24) above, wherein the cancer is selected from the group consisting of colorectal cancer, rectal cancer, breast cancer, non-small-cell lung cancer, non-Hodgkin's lymphoma (NHL), renal cell cancer, prostate cancer, liver cancer, pancreas cancer, soft tissue sarcoma, Kaposi's sarcoma, carcinoid tumor, head and neck cancer, melanoma, ovarian cancer, mesothelioma, and multiple myeloma.

(28) The pharmaceutical composition according to (23) or (24) above, wherein the VEGF-mediated eye disease is at least one selected from age-related macular degeneration, diabetic retinopathy, diabetic macular edema, neovascular glaucoma, retinal vein occlusion, retinopathy of prematurity, choroidal neovascularization associated with pathological myopia, pterygium, rubeosis, pannus, Stevens-Johnson syndrome, and an immunological rejection in a transplanted tissue of the eye.

(29) An angiogenesis inhibitor comprising the monoclonal antibody or the fragment thereof according to any one of (1) to (19) above.

(30) A reagent comprising the monoclonal antibody or the fragment thereof according to any one of (1) to (19) above.

(31) A kit comprising the monoclonal antibody or the fragment thereof according to any one of (1) to (19) above.

(32) A method for treating or preventing a cancer or a VEGF-mediated eye disease, comprising a step of administering to a subject a therapeutically effective amount of the antibody or the fragment thereof according to any one of (1) to (19) above.

(33) The antibody or the fragment thereof according to any one of (1) to (19) above, for use in a method for treating or preventing a cancer or a VEGF-mediated eye disease.

(34) The antibody or the fragment thereof according to any one of (1) to (19) above, for use in the manufacture of a medicament for treatment or prevention of a cancer or a VEGF-mediated eye disease.

Advantageous Effects of Invention

According to the present invention, a novel antibody against VEGF that binds with significantly high affinity compared to the prior art to a vascular endothelial growth factor (VEGF) to inhibit its binding to receptor.

BRIEF DESCRIPTION OF DRAWINGS

FIG. 1 shows the results of examining the capability of inhibiting binding of VEGF to VEGFR2 of the antibody of present invention.

FIG. 2 shows the results of examining the inhibiting effect of the antibody of the present invention on cell proliferation.

FIG. 3 shows the results of examining the in vivo inhibiting effect of KLHa505, that is the antibody of the present invention, on tumor growth.

FIG. 4 shows the results of examining the in vivo inhibiting effect of KLHb1501, that is the antibody of the present invention, on tumor growth.

FIG. 5 shows the results of examining the in vivo inhibiting effect of KLHb1501HC, that is the humanized chimeric antibody of the present invention, on tumor growth.

FIG. 6 shows the results of binding of KLHb1501CC, that is a caninized chimeric antibody of the present invention to canine VEGFA.

FIG. 7 shows the results of examining KLHb1501CC, that is the caninized chimeric antibody of the present invention, for its in vivo inhibiting effect on tumor growth in human-derived cancer cells.

FIG. 8 shows the results of examining the in vivo inhibiting effect of KLHb1501CC, that is the caninized chimeric antibody of the present invention, on tumor growth in a canine-derived cancer cells.

FIG. 9 shows the results of examining KLHa505HC, that is the humanized chimeric antibody of the present invention, for the capability of binding to VEGF165, VEGF121 and VEGF165b.

FIG. 10 shows the results of examining KLHb1501HC, that is the humanized chimeric antibody of the present invention, for the capability of binding to VEGF165, VEGF121 and VEGF165b.

DESCRIPTION OF EMBODIMENTS

The present invention will be described in detail as follows. The following embodiments are merely examples for describing the present invention, and are not intended to limit the present invention only to these embodiments. The present invention can be implemented in various modes without departing from the scope of the invention. Moreover, this description includes the contents as disclosed in the specification and drawings of Japanese Patent Application (Japanese Patent Application No. 2016-001277) filed on Jan. 6, 2016, which is priority document of the present application.

1. Summary

Currently, Avastin is known as an anti-VEGF antibody effective for treatment of cancer and age-related macular degeneration, however, Avastin is known to have low affinity for VEGF.

On the other hand, the present inventors have developed an antibody having significantly high affinity for VEGF compared to the prior art, and thus have discovered that the antibody is effective for suppression of angiogenesis and treatment of cancer.

The present invention has been completed based on these findings.

2. Vascular Endothelial Growth Factor (VEGF)

VEGFs are proteins playing an important role in angiogenesis. VEGFs involve cell division and migration, induction of differentiation, vascular hyperpermeability, activation of monocytes and macrophages, and the like through binding to their receptors to cause intracellular signal transduction.

In the present invention, examples of VEGF include VEGF-A, VEGF-B, VEGF-C, VEGF-D, VEGF-E, PlGF-1, and PlGF-2, and a preferable example thereof is VEGF-A.

VEGF in the present invention may be derived from any mammal. Examples of such a mammal include mice, rats, rabbits, dogs, goats, monkeys and humans, preferably, mice, rats, dogs and humans.

Examples of human VEGF-A include VEGF ($VEGF_{165}$) consisting of 165 amino acid residues, a subtype thereof; that is, VEGF ($VEGF_{121}$) consisting of 121 amino acid residues, VEGF ($VEGF_{145}$) consisting of 145 amino acid residues, VEGF ($VEGF_{183}$) consisting of 183 amino acid residues, VEGF ($VEGF_{189}$) consisting of 189 amino acid residues, VEGF ($VEGF_{206}$) consisting of 206 amino acid residues, VEGF ($VEGF_{165b}$) differing from the above $VEGF_{165}$ in the amino acid sequence of the C-terminal region, and naturally-occurring allelic variants thereof and processing variants thereof. In the present invention, as examples of human VEGF-A, $VEGF_{121}$ and $VEGF_{165}$ are preferred. VEGF is encoded on chromosome 6p12, and the mRNA is 16,272 bp long. VEGF is consisting of exons 1 to 5, and 6a, 6b, 7a, 7b, 8a and 8b. $VEGF_{165}$ binds to all of NRP1, VEGFR1 and VEGFR2.

Furthermore, examples of canine VEGF include, but are not limited to, VEGF ($VEGF_{164}$) consisting of 164 amino acid residues, VEGF ($VEGF_{120}$) consisting of 120 amino acid residues, VEGF ($VEGF_{144}$) consisting of 144 amino acid residues, VEGF ($VEGF_{147}$) consisting of 147 amino acid residues, VEGF ($VEGF_{162}$) consisting of 162 amino acid residues, VEGF ($VEGF_{182}$) consisting of 182 amino acid residues, VEGF ($VEGF_{188}$) consisting of 188 amino acid residues, VEGF ($VEGF_{205}$) consisting of 205 amino acid residues, VEGF ($VEGF_{164b}$) differing from the above $VEGF_{164}$ in the amino acid sequence of the C-terminal region, and naturally occurring allelic variants thereof and processing variants thereof.

In the present invention, the amino acid sequences of mouse, rat, canine and human VEGFs, and $VEGF_{121}$ and $VEGF_{165}$ are represented by SEQ ID NOS: 2, 4, 6, 8, 10, and 12, respectively. Moreover, the base (nucleotide) sequences of DNA encoding mouse, rat, canine and human VEGFs, and $VEGF_{121}$ and $VEGF_{165}$ are represented by SEQ ID NOS: 1, 3, 5, 7, 9 and 11, respectively. These amino acid sequences and nucleotide sequences are each registered in the GenBank database under given Accession Nos.

Mouse VEGF amino acid sequence: NP_001020421.2 (SEQ ID NO: 2)
Rat VEGF amino acid sequence: NP_114024.2 (SEQ ID NO: 4)
Canine VEGF amino acid sequence: NP_001003175 (SEQ ID NO: 6)
Human VEGF-A amino acid sequence: NP_001020537.2 (SEQ ID NO: 8)
$VEGF_{121}$ amino acid sequence: ABO26344.1 (SEQ ID NO: 10)
$VEGF_{165}$ amino acid sequence: AAM03108.1 (SEQ ID NO: 12)

Mouse VEGF-encoding DNA nucleotide sequence: NM_001025250.3 (SEQ ID NO: 1)
Rat VEGF-encoding DNA nucleotide sequence: NM_031836.2 (SEQ ID NO: 3)
Canine VEGF-encoding DNA nucleotide sequence: NM_001003175.2 (SEQ ID NO: 5)
Human VEGF-A-encoding DNA nucleotide sequence: NM_001025366.2 (SEQ ID NO: 7)
$VEGF_{121}$-encoding DNA nucleotide sequence: EF424789.1 (SEQ ID NO: 9)
$VEGF_{165}$-encoding DNA nucleotide sequence: AF486837.1 (SEQ ID NO: 11)

VEGFs to be used in the present invention include the following proteins (a) to (c):
(a) a protein comprising the amino acid sequence represented by SEQ ID NO: 2, 4, 6, 8, 10 or 12;
(b) a protein comprising an amino acid sequence on which one or several amino acids are deleted, substituted or added with respect to the amino acid sequence represented by SEQ ID NO: 2, 4, 6, 8, 10 or 12, and having binding activity to a VEGF receptor; and
(c) a protein comprising an amino acid sequence that has 80% or higher homology (identity) with the amino acid sequence represented by SEQ ID NO: 2, 4, 6, 8, 10 or 12, and having binding activity to a VEGF receptor.

In the present invention, examples of "a protein comprising the amino acid sequence represented by SEQ ID NO: 2, 4, 6, 8, 10 or 12" include a protein consisting of the amino acid sequence represented by SEQ ID NO: 2, 4, 6, 8, 10 or 12.

Furthermore, examples of "an amino acid sequence on which one or several amino acids are deleted, substituted or added with respect to the amino acid sequence represented by SEQ ID NO: 2, 4, 6, 8, 10 or 12" include:
(i) an amino acid sequence on which 1 to 10 (for example, 1 to 5, preferably 1 to 3, more preferably 1 to 2, and further preferably 1) amino acids are deleted with respect to the amino acid sequence represented by SEQ ID NO: 2, 4, 6, 8, 10 or 12;
(ii) an amino acid sequence on which 1 to 10 (for example, 1 to 5, preferably 1 to 3, more preferably 1 to 2, and further preferably 1) amino acids are substituted with other amino acids with respect to the amino acid sequence represented by SEQ ID NO: 2, 4, 6, 8, 10 or 12;
(iii) an amino acid sequence on which (for example, 1 to 5, preferably 1 to 3, more preferably 1 to 2, and further preferably 1) amino acids are added with respect to the amino acid sequence represented by SEQ ID NO: 2, 4, 6, 8, 10 or 12; and (iv) an amino acid sequence mutated as a combination of (i) to (iii) above.

In the present invention, "VEGF receptor" is at least one VEGF receptor selected from the group consisting of vascular endothelial growth factor receptor-1 (VEGFR1 (another name: Flt-1)), vascular endothelial growth factor receptor-2 (VEGFR2 (another name: KDR)) and vascular endothelial growth factor receptor-3 (VEGFR3), and is preferably vascular endothelial growth factor receptor-1 (VEGFR1) and/or vascular endothelial growth factor receptor-2 (VEGFR2), and more preferably vascular endothelial growth factor receptor-2 (VEGFR2). Moreover, the term "binding activity to a VEGF receptor" means activity of specifically binding to a VEGF receptor. The presence or the absence of the binding activity can be determined using a known method, such as immunological techniques including immunoprecipitation, Western blotting, EIA (enzyme immunoassay), ELISA (enzyme-linked immunosorbent assay) and the like or pull-down assay. Furthermore, the term "binding activity to a VEGF receptor" means having at least 10% or more, 20% or more, 30% or more, 40% or more, 50% or more, 60% or more, 70% or more, 80% or more, and preferably 90% or more activity, when compared to the activity of the protein consisting of the amino acid sequence represented by SEQ ID NO: 2, 4, 6, 8, 10 or 12, which is set to 100%.

Furthermore, examples of VEGF in the present invention include, in addition to a protein having the amino acid sequence represented by SEQ ID NO: 2, 4, 6, 8, 10 or 12, a protein having an amino acid sequence that has 80% or more homology (identity) with the amino acid sequence represented by SEQ ID NO: 2, 4, 6, 8, 10 or 12, and having binding activity to a VEGF receptor. Examples of such a protein also include a protein having an amino acid sequence that has about 80% or more, 85% or more, 90% or more, 95% or more, 96% or more, 97% or more, 98% or more, or 99% or more homology with the amino acid sequence represented by SEQ ID NO: 2, 4, 6, 8, 10 or 12, and having binding activity to a VEGF receptor (an amino acid sequence substantially equivalent to the amino acid sequence represented by SEQ ID NO: 2, 4, 6, 8, 10 or 12). Homology can be determined using a homology search site on the Internet, for example, by performing a homology search program such as FASTA, BLAST, PSI-BLAST or the like on the DNA Data Bank of Japan (DDBJ). Homology search can also be performed using BLAST on the National Center for Biotechnology Information (NCBI).

Mutagenesis of DNA encoding the relevant protein in order to prepare a protein having the above mutation can be performed using a kit for mutagenesis using site-directed mutagenesis such as Kunkel method, Gapped duplex method or the like, such as QuikChange™ Site-Directed Mutagenesis Kit (Stratagene), GeneTailor™ Site-Directed Mutagenesis System (Invitrogen), TaKaRa Site-Directed Mutagenesis System (Mutan-K, Mutan-Super Express Km and the like: Takara Bio) or the like. Moreover, a method such as a site-directed mutagenesis method described in "Molecular Cloning, A Laboratory Manual (4th edition)" (Cold Spring Harbor Laboratory Press (2012)) can be used.

3. Antibody Against VEGF

In the present invention, the term "antibody against VEGF" (hereafter, may also be referred to as "anti-VEGF antibody".) refers to an antibody that specifically binds to the above VEGF. The anti-VEGF antibody of the present invention binds to VEGF with high affinity compared to the prior art to inhibit binding of VEGF to a VEGF receptor (VEGFR).

Note that, bevacizumab (Avastin®) that is well known as an anti-VEGF antibody is known to have a dissociation constant of 47.9 nmol/L for binding to VEGF.

In the present invention, the term "inhibit binding" does not always means 100% inhibition of the binding of VEGF to the VEGFR. The antibody of the present invention inhibits binding of VEGF to the VEGFR, for example, 50% or more, preferably 60% or more, 70% or more, 80% or more, 90% or more, 95% or more, 96% or more, 97% or more, 98% or more, and 99% or more thereof.

An inhibiting effect on the binding can be evaluated using a known method for a binding inhibition test, such as a method used in Example 2 of the Description.

The antibody of the present invention is a neutralizing antibody that neutralizes VEGF specific activity through its specific binding to VEGF. In the present invention, the term "specifically bind to" means binding to (reacting with) a target molecule, but substantially not binding (not reacting with)

molecules other than the target molecule. Furthermore, in the present invention, the term "neutralize" at least means to inhibit (suppress) the activity of VEGF to bind to VEGFR. Whether or not binding is specific can be confirmed by immunological techniques, such as ELISA, Western blot method or immunohistological staining.

Hereafter, a method for preparing an anti-VEGF antibody is described.

(1) Preparation of Antigen

VEGF is used as an immunogen for preparing the antibody of the present invention.

When VEGF is used as an immunogen, a peptide comprising an amino acid sequence that is a portion of the full length sequence of VEGF can also be used. VEGF to be used as an antigen or an immunogen and methods for introducing mutations are as described in the above "2. VEGF".

VEGF may be natural VEGF purified from a mouse, rat, dog, or human tissues or cells, for example, or VEGF produced via genetic engineering techniques. For example, a biological sample confirmed to contain VEGF is fractionated into a soluble fraction and an insoluble fraction using various surfactants, such as Triton-X or Sarkosyl. The insoluble fraction is further dissolved in urea, guanidine hydrochloride or the like, and allow to bind to various columns, such as a heparin column or a binding resin, so that VEGF can be obtained. Moreover, VEGF to be used as an antigen can also be synthesized by specifying the amino acid sequence and then using a known protein synthesis method such as a solid phase method or a commercially available protein synthesizer. A synthesized peptide is bound to a carrier protein such as Keyhole Limpet Hemocyanin (KLH) or thyroglobulin and thus the resultant can be used as an immunogen.

(2) Preparation of Polyclonal Antibody

The above-prepared VEGF or a partial peptide alone is administered or the same is administered together with a carrier, a diluent or the like to a non-human mammal, such as a rabbit, a dog, a guinea pig, a mouse, a rat, or a goat for immunization. The dosage of the antigen per animal ranges from 0.1 mg to 10 mg when an adjuvant is used. Examples of the adjuvant include Freund's complete adjuvant (FCA), Freund's incomplete adjuvant (FIA), and an aluminum hydroxide adjuvant. Immunization is performed by mainly intravenous, subcutaneous, intraperitoneal injection, or the like. Furthermore, the immunization interval is not particularly limited, and immunization is performed at intervals of several days to several weeks, and preferably at intervals of 1 to 2 weeks for 2 to 10 times and preferably 3 to 5 times. The immunization interval can be determined by persons skilled in the art considering the resulting antibody titer. Preferably, blood is sampled when subcutaneous immunization is performed 3 to 4 times and then the antibody titer is measured. Antibody titer in serum can be measured by ELISA (enzyme-linked immunosorbent assay), EIA (enzyme immunoassay), radioimmunoassay (RIA) or the like. After confirmation of a sufficient increase in antibody titer, whole blood is collected, and then an antibody can be separated and purified by a generally employed method. Regarding separation and purification, a known method such as an ammonium sulfate salting-out method, ion exchange chromatography, gel filtration chromatography, and affinity chromatography is adequately selected or combined, and then purification can be performed. That is, a serum containing a target antibody is applied to a column to which proteins other than VEGF have been bound, a flow-through fraction is collected, and then a polyclonal antibody having improved specificity to VEGF can be obtained.

(3) Preparation of Monoclonal Antibody (i) Collection of Antibody-Producing Cells In a manner similar to that for preparation of a polyclonal antibody, VEGF or a partial peptide alone or the same together with a carrier or a diluent is administered to a non-human mammal for immunization. The dosage of an antigen per animal, the type of an adjuvant to be used, an immunization method, and immunization intervals are similar to those for preparation of a polyclonal antibody. One to 30 days, and preferably 2 to 5 days after the final immunization date, individuals confirmed to have antibody titers are selected, and then antibody-producing cells are collected. Examples of antibody-producing cells include spleen cells, lymph node cells, and peripheral blood cells, and among them spleen cells or lymph node cells are preferred.

(ii) Cell Fusion

To obtain hybridomas, cell fusion of antibody-producing cells and myeloma cells is performed. Cell fusion procedures can be implemented according to a known method such as the method of Kohler et al. As myeloma cells to be fused to antibody-producing cells, generally available established cell lines of an animal such as a mouse can be used. Cell lines that can be preferably used herein have drug selectivity and have a property of being unable to survive in HAT selective medium (containing hypoxanthine, aminopterin, and thymidine) when the cells are in an unfused state, but able to survive only in a state fused to antibody-producing cells. Examples of myeloma cells include mouse myeloma cell lines such as P3-x63-Ag8U.1, SP2/O-Ag14, PAI, P3U1, NSI/1-Ag4-1, and NSO/1, and rat myeloma cell lines such as YB2/0.

The cell fusion of myeloma cells and antibody-producing cells described above is performed by mixing $1\times10^8$ to $5\times10^8$ antibody-producing cells and $2\times10^7$ to $10\times10^7$ myeloma cells in animal cell culture medium such as serum-free DMEM and RPMI-1640 medium (the cell ratio of antibody-producing cells to myeloma cells ranges from 10:1 to 1:1), and then performing fusion reaction in the presence of a cell fusion accelerator. As a cell fusion accelerator, polyethylene glycol having an average molecular weight of 1000-6000 daltons or Sendai virus can be used, for example. In addition, antibody-producing cells and myeloma cells can be fused using a commercially available cell fusion device utilizing electrical stimulation (for example, electroporation).

(iii) Hybridoma Selection and Cloning

A target hybridoma is selected from cells after cell fusion treatment. Such a method is performed by appropriately diluting a cell suspension with 10% to 20% fetal calf serum-containing RPMI-1640 medium or the like, placing the resultant on a microtiter plate at about 0.3 cells/well as calculated by a limiting dilution method, adding selective medium such as HAT medium to each well, and then culturing while appropriately exchanging selective media. As a result, cells that grow around 10 days after the start of culture in selective media can be obtained as hybridomas.

Next, hybridomas that have grown are further screened. Hybridoma screening may be performed according to a general method and is not particularly limited. For example, a portion of a culture supernatant contained in wells in which hybridomas have been cultured is collected and then can be screened by enzyme immunoassay, radioimmunoassay or the like. As a specific example, an antigen is adsorbed to a 96-well plate, followed by blocking with calf serum. The culture supernatant of hybridoma cells is reacted with an immobilized antigen at 37° C. for 1 hour, and then reacted with peroxidase-labeled anti-mouse IgG at 37° C. for 1 hour, for color development using orthophenylenediamine as a substrate. The reaction is stopped with acid, and then absorbance at a wavelength of 490 nm is measured, so that screening can be performed. Hybridomas producing a monoclonal antibody found positive as a result of the above measurement method is cloned by a limiting dilution method or the like. Finally, hybridomas that are cells producing the monoclonal antibody that specifically binds to VEGF are established.

(iv) Collection of Monoclonal Antibody

As a method for collecting a monoclonal antibody from the thus established hybridomas, a general cell culture method, an ascites formation method, or the like can be employed. According to a cell culture method, the hybridomas are cultured in animal cell culture medium such as 10% fetal calf serum-containing RPMI-1640 medium, MEM, or serum free medium under general culture conditions (for example, 37° C., 5% $CO_2$ concentration) for 7 to 14 days, and then an antibody is obtained from the culture supernatant. According to an ascites formation method, about $5 \times 10^6$ to $2 \times 10^7$ hybridomas are administered intraperitoneally to an animal of the same species as that of a mammal from which myeloma cells are derived, such as mouse (BALB/c), so that hybridomas are grown in large amounts. One to 2 weeks later, ascites is collected. When the above method for collecting an antibody requires purification of the antibody, purification can be performed by appropriately selecting a known method such as an ammonium sulfate salting-out method, ion exchange chromatography, gel filtration, and affinity chromatography, or using these methods in combination.

Examples of the antibody of the present invention include, but are not limited to, an antibody wherein:
a heavy chain variable region (VH) comprises a heavy chain complementarity determining region (CDR)1 (CDR-H1) comprising or consisting of the amino acid sequence represented by SEQ ID NO: 14, heavy chain CDR2 (CDR-H2) comprising or consisting of the amino acid sequence represented by SEQ ID NO: 16, and/or heavy chain CDR3 (CDR-H3) comprising or consisting of the amino acid sequence represented by SEQ ID NO: 18; and/or
a light chain variable region (VL) comprises light chain CDR1 (CDR-L1) comprising or consisting of the amino acid sequence represented by SEQ ID NO: 20, light chain CDR2 (CDR-L2) comprising or consisting of the amino acid sequence that consists of tryptophan (W)-alanine (A)-serine (S) (may also be referred to as "amino acid sequence WAS", "amino acid sequence Trp-Ala-Ser"), and/or light chain CDR3 (CDR-L3) comprising or consisting of the amino acid sequence represented by SEQ ID NO: 22.

In another aspect, examples of the antibody of the present invention include, but are not limited to, an antibody wherein:
a heavy chain variable region comprises heavy chain CDR1 (CDR-H1) comprising or consisting of the amino acid sequence represented by SEQ ID NO: 24, heavy chain CDR2 (CDR-H2) comprising or consisting of the amino acid sequence represented by SEQ ID NO: 26 and/or heavy chain CDR3 (CDR-H3) comprising or consisting of the amino acid sequence represented by SEQ ID NO: 28; and/or
a light chain variable region comprises light chain CDR1 (CDR-L1) comprising or consisting of the amino acid sequence represented by SEQ ID NO: 30, light chain CDR2 (CDR-L2) comprising or consisting of the amino acid sequence that consists of glycine (G)-threonine (T)-asparagine (N) (may also be referred to as "amino acid sequence GTN", "amino acid sequence Gly-Thr-Asn") and/or light chain CDR3 (CDR-L3) comprising or consisting of the amino acid sequence represented by SEQ ID NO: 32.

In another aspect, examples of the antibody of the present invention include, but are not limited to, an antibody wherein: the amino acid sequence of a heavy chain variable region comprises or consists of the amino acid sequence represented by SEQ ID NO: 34 or 38; and/or the amino acid sequence of a light chain variable region comprises or consists of the amino acid sequence represented by SEQ ID NO: 36 or 40.

(4) Preparation of Recombinant Antibody

A preferred aspect of the antibody of the present invention is a recombinant antibody. Examples of the recombinant antibody include, but are not limited to, a chimeric antibody, a humanized antibody, and a caninized antibody.

A chimeric antibody refers to an antibody prepared by linking immunoglobulin gene fragments of animals of different species. In the present invention, examples of a chimeric antibody include a humanized chimeric antibody, and a caninized chimeric antibody, but the types of animals, from which chimeric antibody variable and constant regions are derived, are not limited. A humanized chimeric antibody is an antibody prepared by linking (joining) a mouse-derived antibody variable region to a human-derived constant region, for example (see Proc. Natl. Acad. Sci. U.S.A. 81, 6851-6855, (1984), for example). A caninized chimeric antibody is an antibody prepared by linking a mouse-derived antibody variable region to a dog-derived constant region, for example. When a chimera is prepared, this can be easily constructed by gene recombination techniques so that an antibody prepared through such ligation can be obtained. Here, examples of a mouse-derived antibody variable region include, but are not limited to, a heavy chain variable region comprising or consisting of the amino acid sequence represented by SEQ ID NO: 34 or 38, and a light chain variable region comprising or consisting of the amino acid sequence represented by SEQ ID NO: 36 or 40.

When a humanized antibody is prepared, a technique referred to as, namely, CDR grafting, can be employed. CDR grafting is a method for preparing a reconstructed variable region, whereby a complementarity determining region (CDR) is grafted from a mouse antibody variable region to a human variable region, so that the framework region (FR) is human-derived and CDR is mouse-derived. Next, such humanized reconstructed human variable region is ligated to a human constant region. Such a method for preparing a humanized antibody is known in the art (see e.g., Nature, 321, 522-525 (1986); J. Mol. Biol., 196, 901-917 (1987); Queen C et al., Proc. Natl. Acad. Sci. USA, 86: 10029-10033 (1989); and Japanese Patent No. 2828340).

Here, examples of the amino acid sequence of mouse-derived CDR, which can be used for the humanized antibody of the present invention include, but are not limited to,
CDR1-3 of a heavy chain variable region (CDR-H1, CDR-H2 and CDR-H3) comprising or consisting of the amino acid sequences represented by SEQ ID NO: 14, 16 and 18, respectively,
CDR1-3 of a light chain variable region (CDR-L1, CDR-L2 and CDR-L3) comprising or consisting of the amino acid sequence represented by SEQ ID NO: 20, the amino acid sequence that consists of tryptophan (W)-alanine (A)-serine (S) (amino acid sequence Trp-Ala- Ser), and/or the amino acid sequence represented by SEQ ID NO: 22, respectively.

In another aspect, examples of the amino acid sequences of mouse-derived CDRs that can be used for the humanized antibody of the present invention include, but are not limited to, CDR1-3 of a heavy chain variable region (CDR-H1, CDR-H2 and CDR-H3) comprising or consisting of the amino acid sequences represented by SEQ ID NO: 24, 26, and 28, respectively, CDR1-3 of a light chain variable region (CDR-L1, CDR-L2 and CDR-L3) comprising or consisting of the amino acid sequence represented by SEQ ID NO: 30, the amino acid sequence that consists of glycine (G)-threonine (T)-asparagine (N) (amino acid sequence Gly-Thr-Asn), and/or the amino acid sequence represented by SEQ ID NO: 32, respectively.

A caninized antibody can also be prepared by a technique similar to the above method for preparing a humanized antibody.

In the present invention, examples of a human heavy chain constant region that can be used for a chimeric antibody and a humanized antibody include, but are not limited to, a human heavy chain constant region comprising an amino acid sequence derived from a human IgG1 heavy chain constant region, and for example, a human heavy chain constant region comprising or consisting of the amino acid sequence represented by SEQ ID NO: 42, and examples of a human light chain constant region include, but are not limited to, a human light chain constant region comprising an amino acid sequence derived from a human IgG1 light chain constant region, and for example, a human light chain constant region comprising or consisting of the amino acid sequence represented by SEQ ID NO: 44. Furthermore, examples of DNA encoding a human heavy chain constant region include, but are not limited to, DNA comprising or consisting of the nucleotide sequence represented by SEQ ID NO: 41. Examples of DNA encoding a human light chain constant region include, but are not limited to, DNA comprising or consisting of the nucleotide sequence represented by SEQ ID NO: 43.

Furthermore, in the present invention, examples of a canine heavy chain constant region that can be used for a chimeric antibody and a caninized antibody include, but are not limited to, a canine heavy chain constant region comprising an amino acid sequence derived from the canine IgGB heavy chain constant region, and for example, a canine heavy chain constant region comprising or consisting of the amino acid sequence represented by SEQ ID NO: 46. Moreover, examples of a canine light chain constant region that can be used for a chimeric antibody and a caninized antibody include, but are not limited to, a canine light chain constant region comprising an amino acid sequence derived from a canine Ig light chain (κ chain) constant region or an amino acid sequence derived from a canine Ig light chain (λ chain) constant region, and for example, a canine light chain (κ chain) constant region comprising or consisting of the amino acid sequence represented by SEQ ID NO: 48, or a canine light chain (λ chain) constant region comprising or consisting of the amino acid sequence represented by SEQ ID NO: 50. Moreover, examples of DNA encoding a canine heavy chain constant region include, but are not limited to, DNA comprising or consisting of the nucleotide sequence represented by SEQ ID NO: 45. Examples of DNA encoding a canine light chain (κ chain or λ chain) constant region include, but are not limited to, DNA comprising or consisting of the nucleotide sequence represented by SEQ ID NO: 47 or 49.

In the present invention, a chimeric antibody, a humanized antibody, and a caninized antibody can be prepared according to the above-mentioned known method using a hybridoma or DNA, RNA or the like extracted from the hybridoma as a raw material.

Furthermore, the antibody of the present invention in the form of a fusion protein can be prepared according to a known gene recombination technique using antibody variable regions and another protein. The fusion protein can also be prepared by cross-linking a monoclonal antibody and another protein using a cross-linker.

(5) Preparation of Antibody Fragment

A fragment of the antibody against VEGF to be used in the present invention specifically binds to VEGF.

An antibody fragment refers to a polypeptide containing a partial region of the antibody of the present invention. As an antibody fragment, an antigen-binding fragment is preferred. Examples of the antigen-binding fragment include, but are not limited to, single-chain antibodies (scFv (single chain Fv)), sc (Fv)$_2$), double-chain antibodies (Fab, Fab', diabody (diabody (dibodies), dsFv), and F(ab')$_2$. The above antibody fragment can be obtained by cleaving the antibody of the present invention with various proteases depending on purposes.

For example, Fab can be obtained by treating an antibody molecule with papain, and F (ab')$_2$ can be obtained by treating an antibody molecule with pepsin. Moreover, Fab' can be obtained by cleaving the disulfide bond of the above F(ab)$_2$ hinge region.

In the case of scFv, cDNA encoding antibody H chain V region and L chain V region is obtained and then DNA encoding scFv is constructed. The DNA is inserted into an expression vector, and then the expression vector is introduced into a host organism for expression, so that scFv can be produced.

In the case of a diabody, cDNA encoding antibody H chain V region and L chain V region is obtained, and then DNA encoding scFv is constructed so that a peptide linker has an amino acid sequence with a length of 8 or less residues. The DNA is inserted into an expression vector, and then the expression vector is introduced into a host organism for expression, so that a diabody can be produced.

In the case of dsFv, cDNA encoding antibody H chain V region and L chain V region is obtained, and then DNA encoding dsFv is constructed. The DNA is inserted into an expression vector, and then the expression vector is introduced into a host organism for expression, so that dsFv can be produced.

In the present invention, examples of the nucleotide sequence of DNA encoding a heavy chain variable region include, but are not limited to, DNA comprising or consisting of the nucleotide sequence represented by SEQ ID NO: 33 or 37, and examples of the nucleotide sequence of DNA encoding a light chain variable region include, but are not limited to, DNA comprising or consisting of the nucleotide sequence represented by SEQ ID NO: 35 or 39.

Specific examples of the antibody fragment of the present invention include, but are not limited to, an antibody fragment comprising:

a heavy chain variable region (VH) that comprises heavy chain CDR1 (CDR-H1) comprising or consisting of the amino acid sequence represented by SEQ ID NO: 14, heavy chain CDR2 (CDR-H2) comprising or consisting of the amino acid sequence represented by SEQ ID NO:

16, and/or heavy chain CDR3 (CDR-H3) comprising or consisting of the amino acid sequence represented by SEQ ID NO: 18; and/or a light chain variable region (VL) that comprises light chain CDR1 (CDR-L1) comprising or consisting of the amino acid sequence represented by SEQ ID NO: 20, light chain CDR2 (CDR-L2) comprising or consisting of the amino acid sequence that consists of tryptophan (W)-alanine (A)-serine (S) (amino acid sequence Trp-Ala-Ser) and/or light chain CDR3 (CDR-L3) comprising or consisting of the amino acid sequence represented by SEQ ID NO: 22.

In another aspect, specific examples of the antibody fragment of the present invention include, but are not limited to, an antibody fragment comprising: a heavy chain variable region comprises heavy chain CDR1 (CDR-H1) comprising or consisting of the amino acid sequence represented by SEQ ID NO: 24, heavy chain CDR2 (CDR-H2) comprising or consisting of the amino acid sequence represented by SEQ ID NO: 26 and/or heavy chain CDR3 (CDR-H3) comprising or consisting of the amino acid sequence represented by SEQ ID NO: 28, and/or a light chain variable region comprises light chain CDR1 (CDR-L1) comprising or consisting of the amino acid sequence represented by SEQ ID NO: 30, light chain CDR2 (CDR-L2) comprising or consisting of the amino acid sequence that consists of glycine (G)-threonine (T)-asparagine (N) (amino acid sequence Gly-Thr-Asn), and/or light chain CDR3 (CDR-L3) comprising or consisting of the amino acid sequence represented by SEQ ID NO: 32.

Moreover, examples of the antibody fragment of the present invention include, but are not limited to, an antibody fragment wherein a heavy chain variable region comprises or consists of the amino acid sequence represented by SEQ ID NO: 34 or 38, and/or a light chain variable region comprises or consists of the amino acid sequence represented by SEQ ID NO: 36 or 40.

An antibody fragment (peptide) comprising CDR is composed of at least one region of VH or VL CDRs (CDR1-3). An antibody fragment comprising a plurality of CDRs can be bound directly or via an appropriate peptide linker. An antibody fragment comprising CDR can be produced by constructing DNA encoding antibody VH and VL CDRs, inserting the DNA into a prokaryotic expression vector or a eukaryotic expression vector, and then introducing the expression vector into prokaryotes or eukaryotes for expression. Furthermore, a peptide comprising CDR can also be produced by a chemical synthesis method such as a Fmoc method (fluorenylmethyloxycarbonyl method) and a tBoc method (t-butyloxycarbonyl method).

Examples of DNA encoding VH CDR1-3 include, but are not limited to, DNA comprising or consisting of the nucleotide sequence represented by SEQ ID NO: 13, DNA comprising or consisting of the nucleotide sequence represented by SEQ ID NO: 15 and DNA comprising or consisting of the nucleotide sequence represented by SEQ ID NO: 17, respectively. Examples of DNA encoding VL CDR1-3 include, but are not limited to, DNA comprising or consisting of the nucleotide sequence represented by SEQ ID NO: 19, DNA comprising or consisting of the nucleotide sequence that consists of thymine (T)-guanine (G)-guanine (G)-guanine (G)-cytosine (C)-adenine (A)-thymine (T)-cytosine (C)-cytosine (C) (also referred to as "nucleotide sequence TGGGCATCC"), and DNA comprising or consisting of the nucleotide sequence represented by SEQ ID NO: 21, respectively.

In another aspect, examples of DNA encoding VH CDR1-3 include, but are not limited to, DNA comprising or consisting of the nucleotide sequence represented by SEQ ID NO: 23, DNA comprising or consisting of the nucleotide sequence represented by SEQ ID NO: 25 and DNA comprising or consisting of the nucleotide sequence represented by SEQ ID NO: 27, respectively. Examples of DNA encoding VL CDR1-3 include, but are not limited to, DNA comprising or consisting of the nucleotide sequence represented by SEQ ID NO: 29, DNA comprising or consisting of the nucleotide sequence that consists of guanine (G)-guanine (G)-thymine (T)-adenine (A)-cytosine (C)-cytosine (C)-adenine (A)-adenine (A)-cytosine (C) (may also be referred to as "nucleotide sequence GGTACCAAC"), and DNA comprising or consisting of the nucleotide sequence represented by SEQ ID NO: 31, respectively.

(6) Binding Affinity

Binding affinity can be determined by the binding constant (KA) and dissociation constant (KD). Affinity equilibrium constant (K) is expressed by the ratio of the KA/KD. Its binding affinity can be detected as follows.

Binding constant (KA) and dissociation constant (KD) can be measured using surface plasmon resonance (SPR), and known devices and methods for detecting binding rates in real time and monitoring can be employed (e.g. Biacore®-3000 (GE Healthcare), ProteON XPR36 (Bio-Rad), etc.).

The antibody of the present invention can inhibit its target with an IC50 of $1\times10^{-7}$ mol/L or less (for example, $1\times10^{-7}$ mol/L or less, $1\times10^{-8}$ mol/L or less, $1\times10^{-9}$ mol/L or less, preferably $1\times10^{-10}$ mol/L or less, more preferably $1\times10^{-11}$ mol/L or less).

The present invention provides an antibody that binds to a site to which the antibody against VEGF of the present invention binds. In detail, examples of the antibody against VEGF of the present invention include an antibody that binds to a site, to which a monoclonal antibody against VEGF that binds to VEGF with a dissociation constant of $1\times10^{-11}$ mol/L or less.

A site to which the anti-VEGF antibody of the present invention binds is not limited, as long as it is at least a partial region of VEGF that is an antigen. Examples of a site to which the anti-VEGF antibody of the present invention binds include, at least one region selected from the group consisting of exon 1, 2, 3, 4, 5, 6a, 6b, 7a, 7b, and 8a, and exon 1 to 5 regions are preferred. Persons skilled in the art can specify exon 1 to 5 regions of various VEGFs based on known information such as Genbank. For example, the amino acid sequences of mouse, rat, canine, human VEGF exon 1 to 5 are represented by SEQ ID NO: 51, 52, 53 and 54, respectively.

Persons skilled in the art can specify sites (e.g., regions and epitopes) or polypeptides containing them, to which the anti-VEGF antibody of the present invention binds, based on the Description and known techniques such as epitope mapping or X-ray structural analysis.

Furthermore, an antibody that binds to a site, to which the above monoclonal antibodies bind, may be a polyclonal antibody or a monoclonal antibody. When such an antibody is a monoclonal antibody, the antibody may be a recombinant antibody, such as a chimeric antibody, a humanized antibody, or a caninized antibody.

An antibody that binds to a site, to which the antibody against VEGF of the present invention binds, competes with the antibody against VEGF of the present invention for binding with VEGF. Persons skilled in the art can understand that an antibody competing with the antibody against VEGF of the present invention for binding with VEGF has specificity and/or activity equivalent to that of the antibody of the present invention (Specifically, a monoclonal antibody against VEGF, which binds to VEGF with a dissociation constant of $1\times10^{-11}$ mol/L or less).

A competition test using an antibody is a technique established in the technical field of antibodies as a technique for examining if a set of antibodies bind to the same (or redundant) site (see e.g., Ju-Won Kwak et al., Journal of Immunological Methods 191 (1996) 49-54). In the competition test, when the binding of the antibody against VEGF of the present invention is competitively inhibited by an anti-VEGF antibody to be tested, the test subject anti-VEGF antibody can be identified to be an antibody that binds to a site, to which the antibody against VEGF of the present invention binds. Furthermore, the test method does not require information about the structure of the relevant site for examining if a set of antibodies bind to the same (or redundant) site.

That is, persons skilled in the art can obtain an antibody binding to a site, to which the antibody against VEGF of the present invention binds, by conducting a competition test using the antibody against VEGF of the present invention without excessive experimentation.

4. Pharmaceutical Composition

The pharmaceutical composition of the present invention comprises the antibody or a fragment thereof described in the above "3. Antibody against VEGF" as an active ingredient, and is used for a target disease. The pharmaceutical composition of the present invention is used for prevention or treatment of target diseases and is effective for the prevention or the treatment.

Diseases targeted by the pharmaceutical composition of the present invention are not limited, as long as they are VEGF-associated diseases (including symptoms (conditions)), and examples of such diseases include solid tumors, cancers including particularly problematic metastatic tumors, and VEGF-mediated eye diseases, and other immune diseases.

Tumor vascular structures are known to supply blood, and also function as a vascular niche environment supporting cancer stem cells. The vascular niche environment refers to an environment involving maintenance, proliferation and differentiation of hematopoietic stem cells that are sources of blood and blood vessels, and is considered to be important for cancer stem cell proliferation.

Unlike normal cells, cancer cells are characterized by high proliferative ability, unlimited number of cell divisions, and ability to cause invasion and metastasis to peripheral tissues. In recent years, it has become considered that not all cancer cells in a cancer tissue have such properties, and limited partial cells have such properties. That is, these partial cancer cells are cells having properties observed in common among stem cells such as embryonic stem cells and somatic stem cells, including self-replicating ability, by which the cells can create cells completely identical thereto, and pluripotency, by which the cells are capable of differentiating into many cell types. The partial cancer cells are considered to be cancer stem cells that function as a source for creating the majority of peripheral cancer cells via differentiation while maintaining cells identical to themselves in the cancer tissue through self-replication.

Cancer stem cells are considered to be a major cause of cancer recurrence and cancer metastasis, and thus importance of targeting cancer stem cells in cancer treatment has been indicated. If significant inhibition of cancer stem cell proliferation within tumor tissue becomes possible, a novel treatment capable of killing entire cancer cells effectively can be developed.

The term "cancer stemness" in the present invention refers to a property of a cell population exerting the properties of cancer stem cells. Specifically, cancer stemness refers to properties of having self-replication and pluripotency peculiar to stem cells, and a property of cells functioning as a source of cancer.

In the present invention, examples of cancer include brain tumor, cervical cancer, esophageal cancer, cancer on the tongue, lung cancer, breast cancer, pancreatic cancer, gastric cancer, cancer of small bowel, duodenal cancer, colon cancer, bladder cancer, renal cancer, liver cancer, prostate cancer, uterine cancer, uterine cervix cancer, ovarian cancer, thyroid cancer, gallbladder cancer, pharyngeal cancer, sarcoma, melanoma, leukemia, lymphoma, and multiple myeloma.

In the present invention, VEGF-mediated eye disease is VEGF-associated disease that is caused by pathological angiogenesis or vascular hyperpermeability in the eye. That is, the VEGF-mediated eye disease can be treated or prevented by inhibiting binding of VEGF to a VEGF receptor using the anti-VEGF antibody. Examples of such disease include age-related macular degeneration (including special types such as polypoidal choroidal vasculopathy and retinal angiomatous proliferation), diabetic retinopathy, diabetic macular edema, neovascular glaucoma, retinal vein occlusion, retinopathy of prematurity, choroidal neovascularization associated with pathological myopia, pterygium, rubeosis, pannus, Stevens-Johnson syndrome, and immunological rejection of transplanted tissue (e.g., corneal tissue) of the eye.

In the present invention, the term "pathological angiogenesis" refers to angiogenesis that takes place, in morbidity or a state inducing morbidity, when new blood vessels grow excessively, insufficiently, or inappropriately (for example, the position or timing is undesirable from a medical viewpoint, or in development) compared with normal physiological angiogenesis (vasculogenesis).

In the present invention, the term "treatment", "treat", or "treating" refers to contacting (for example, administrating) the antibody or a fragment thereof or the pharmaceutical composition of the present invention (hereafter, may also be referred to as "the pharmaceutical composition of the present invention or the like") with a subject after the onset of the disease, thereby alleviating the symptoms of the disease, compared to when the subject is not contacted with the pharmaceutical composition of the present invention or the like. The treatment as used herein does not always refer to completely suppressing the symptoms of a disease. The term "onset of a disease" refers to the appearance of the symptoms of the disease in the body.

In the present invention, the term "prevention", "prevent", or "preventing" refers to contacting (for example, administrating) the pharmaceutical composition of the present invention or the like with a subject before the onset of a disease, thereby alleviating symptoms of the disease after the onset of the disease, compared to when the subject is not contacted with the pharmaceutical composition of the present invention or the like. The term "prevention" does not always refer to completely suppressing the onset of the disease.

The pharmaceutical composition of the present invention can comprise, in addition to the antibody against VEGF of the present invention, a pharmaceutically acceptable carrier. The term "pharmaceutically acceptable carrier" refers to any carrier (e.g., liposome, lipid microcapsule, and micelle), diluent, excipient, wetting agent, buffering agent, suspending agent, lubricant, adjuvant, emulsifier, disintegrator, absorbent, preservative, surfactant, colorant, flavoring, or sweetener appropriate for the pharmaceutical composition for immune diseases.

The pharmaceutical composition of the present invention or the like can be formulated into preparations for injection, freeze-dried products, tablets, hard capsules, soft capsules, granules, powders, pills, syrups, suppositories, cataplasm, ointments, cream pharmaceuticals, eye drops, and the like. Liquid preparations such as preparations for injection may be in the form of powder to be prepared before use (for example, freeze-dried powder), which is dissolved in saline or the like before use.

The pharmaceutical composition of the present invention or the like can be administered topically or systemically through any means known by persons skilled in the art. The route of administration of the pharmaceutical composition of the present invention can be oral administration and parenteral administration. In the case of parenteral administration, intratissue administration (e.g., subcutaneous administration, intraperitoneal administration, intramuscular administration, and intravenous administration), intradermal administration, local administration (e.g., transdermal administration) or transrectal administration can be performed. The pharmaceutical composition of the present invention can be administered in dosage forms appropriate for these routes of administration.

The dosage of the pharmaceutical composition of the present invention or the like can be varied depending on factors such as a subject's age, body weight, health status, gender, and symptoms, and the animal species of a subject, the route of administration, the frequency of administration, and a dosage form, and specific procedures for administration can be determined by persons skilled in the art. The dosage of the antibody of the present invention for treatment of cancer ranges from, for example, 0.1 mg to 100 mg/day, preferably 1 mg to 15 mg/day, and more preferably 2 mg to 12 mg/day per kg body weight of a subject, but the examples are not limited thereto. Regarding the frequency of administration, the pharmaceutical composition can be administered once to 5 times a day. The dosage of the antibody of the present invention for treatment of VEGF-mediated eye disease ranges from, for example, 0.01 mg to 100 mg/eye, and more preferably, 0.1 mg to 10 mg/eye. Regarding the frequency of administration, the antibody can be administered once a day to once every two months, but the examples are not limited thereto.

The timing of administration can be appropriately determined depending on symptoms, and several dosages can be administered simultaneously or separately at intervals. Furthermore, the pharmaceutical composition of the present invention may be administered to a subject before the onset of a disease or after the onset of the disease.

The pharmaceutical composition of the present invention can be administered to a mammal as a subject. Examples of mammals include mice, rats, hamsters, guinea pigs, rabbits, cats, dogs, goats, pigs, sheep, cattle, horses, monkeys, and humans.

5. Method for Treating or Preventing a Cancer or a VEGF-Mediated Eye Disease

According to the present invention, a cancer or a VEGF-mediated eye disease can be treated or prevented by administrating to a subject the antibody against VEGF or a fragment thereof or the pharmaceutical composition comprising the same. That is, the present invention provides a method for treating or preventing a cancer or a VEGF-mediated eye disease, comprising a step of administering to a subject a therapeutically effective amount of the antibody of the present invention or a fragment thereof or the pharmaceutical composition comprising the same. The therapeutically effective amount of the antibody of the present invention or a fragment thereof or the pharmaceutical composition comprising the same is varied depending on factors such as a subject's age, body weight, health status, gender, and symptoms, the route of administration, the frequency of administration, and a dosage form. Persons skilled in the art can easily determine the therapeutically effective amount required for treatment or prevention of a cancer or a VEGF-mediated eye disease. In the present invention, "subject" includes subjects in need of treatment or prevention of a cancer or a VEGF-mediated eye disease. In addition, mammals to be subjected to treatment or prevention as "subject" are as described above.

In the method for treating or preventing a cancer or a VEGF-mediated eye disease of the present invention, "cancer", "VEGF-mediated eye disease", "treatment" and "prevention" are as described above. Moreover, the dosage form, the route of administration, the dosage, the timing of administration and the like of the antibody of the present invention or a fragment thereof or the pharmaceutical composition comprising the same are also as described above.

6. Angiogenesis Inhibitor

The antibody of the present invention inhibits binding of VEGF to a VEGF receptor, and thus can inhibit angiogenesis resulting from the binding. Thus, the present invention provides an angiogenesis inhibitor comprising the antibody or a fragment thereof described in the above "3. Antibody against VEGF" as an active ingredient.

The angiogenesis inhibitor of the present invention can be used as a reagent or used for treatment of a mammal, and its dosage form, additives, route of administration, administration target, dosage and the like can be appropriately selected according to the description of the above "4. Pharmaceutical composition". However, the angiogenesis inhibitor of the present invention may be an inhibitor comprising the antibody of the present invention or a fragment thereof alone.

7. Use of Antibody

The antibody of the present invention or a fragment thereof can be used in a method for treating or preventing a cancer or a VEGF-mediated eye disease, or the manufacture of a medicament for treatment or prevention of a cancer or a VEGF-mediated eye disease. Specifically, the present invention provides the anti-VEGF antibody of the present invention or a fragment thereof for use in the method for treating or preventing a cancer or a VEGF-mediated eye disease. Moreover, the present invention provides the anti-VEGF antibody of the present invention or a fragment thereof for use in the manufacture of a medicament for treatment or prevention of a cancer or a VEGF-mediated eye disease. Furthermore, the present invention provides the anti-VEGF antibody or a fragment thereof for use in the manufacture of an angiogenesis inhibitor.

In these aspects, "cancer", "VEGF-mediated eye disease", "treatment" and "prevention" are as described above.

8. Combination Therapy

The pharmaceutical composition of the present invention can be used for administration in combination with at least one of other anticancer agents. Examples of anticancer agents to be used in the present invention include sorafenib (Nexavar®), sunitinib (Sutent®), bevacizumab (Avastin®), cisplatin (cDDP), carboplatin (Paraplatin®), paclitaxel (Taxol®), docetaxel (Taxotere®), gemcitabine hydrochloride (Gemzar®), gefitinib (Iressa®), erlotinib (Tarceva®), irinotecan hydrochloride (CPT-11), and 5-fluorouracil (5-FU).

It can be expected that combined administration of the pharmaceutical composition of the present invention and at least one of anticancer agents exert more advantageous effects than an independent use thereof. Such advantageous effects include an effect on alleviating adverse effects more than conventional therapies while maintaining the therapeutic effects.

The term "used in combination" in the present invention refers to simultaneous administration of or separate administration of the pharmaceutical composition of the present invention and at least one of the above anticancer agents. The term "simultaneously" means that administration is performed at the same timing in a single administration schedule, but the times; that is, hours and minutes of administration are not required to be completely the same. The term "separately" means that administration is performed at different timings in a single administration schedule.

The dosage form, the route of administration, and the administration target of the pharmaceutical composition or the like and an anticancer agent to be used for combination therapy in the present invention are not particularly limited, and can be appropriately selected according to the description of the above "4. Pharmaceutical composition". Moreover, the dosage forms or dosages of agents to be used in combination may differ from each other, and can be appropriately adjusted depending on a combination employed.

When the pharmaceutical composition of the present invention is used in combination with another anticancer agent, the dosage can be decreased as appropriate. Therefore, when the pharmaceutical composition of the present invention is combined with another anticancer agent, the following combinations of (i) an effective dose of the pharmaceutical composition of the present invention and an effective dose of another anticancer agent,
(ii) an effective dose of the pharmaceutical composition of the present invention and a subeffective dose of another anticancer agent,
(iii) a subeffective dose of the pharmaceutical composition of the present invention and an effective dose of another anticancer agent, and
(iv) a subeffective dose of the pharmaceutical composition of the present invention and a subeffective dose of another anticancer agent can be employed.

Even in an aspect in which one of or both the pharmaceutical composition and an anticancer agent are used in subeffective doses, the two can be administered in combination in such an aspect, when the combination can exert pharmacological effects.

9. Reagent, Kit

The monoclonal antibody of the present invention or a fragment thereof can be included in a reagent for detection of VEGF or a kit. That is, the present invention provides a reagent and a kit comprising the monoclonal antibody of the present invention or a fragment thereof. The reagent and the kit of the present invention can be used as a reagent for detecting VEGF or a kit, for example.

In the reagent and the kit of the present invention, the monoclonal antibody of the present invention or a fragment thereof may be treated by a method such as freezing for easy handling, and then directly or mixed with a known pharmaceutically acceptable carrier, such as an excipient, an extending agent, a binder, and a lubricant, and a known additive (including a buffering agent, a tonicity agent, a chelating agent, a colorant, a preservative, an aroma chemical, a flavoring agent, a sweetening agent and the like), for example.

The kit of the present invention can comprise, in addition to the monoclonal antibody of the present invention or a fragment thereof, a buffer, an enzyme solution, a secondary antibody, a solution for dilution, instructions, and the like.

Hereafter, the present invention is described in detail by the Examples, but the present invention is not limited to the Examples.

Example 1

Preparation of Monoclonal Antibody
(1) Preparation of Antigen

Human recombinant $VEGF_{165}$ (hereafter, may also be referred to as "VEGF", "$rhVEGF_{165}$" or "rhVEGF") expressed by CHO cells (PROSPEC) was used as an antigen. For the purpose of suppressing the effect of VEGF on mice, an antigen bound to KLH (Keyhole Limpet Hemocyanin) was prepared. In this case, VEGF and KLH were mixed so that the molar ratio of VEGF to KLH was 4:1 in PBS (−) (0.01 M sodium-phosphate buffer, 0.138 M NaCl, 0.0027 M KCl, pH 7.4), and then 1% glutaraldehyde was added, and then the mixture was allowed to react at room temperature for 1 hour, thereby cross-linking KLH and $rhVEGF_{165}$. The thus prepared protein may also be referred to as "KLH-VEGF" in the followings.

(2) Immunization rhVEGF or KLH-VEGF and Freund's complete adjuvant were mixed in equal amounts, and then the mixture was administered intraperitoneally to BALB/c mice in an amount of 100 μl (about 40 μg/mouse). Subsequently, about 40 μg of KLH-VEGF or rhVEGF was administered with an incomplete Freund's adjuvant intraperitoneally to mice once every 3 weeks for boosters (additional immunization). Boosters were performed not more than 12 times. Final immune stimulation was performed by administering saline containing about 40 μg of KLH-VEGF or rhVEGF into the tail vein of each mouse on day 3 before splenectomy.

(3) Cell Fusion

Isolated splenocytes and a mouse myeloma cell line, P3-x63-Ag8U. 1 (DS PHARMA BIOMEDICAL), were mixed at 5:1 in terms of the number of cells, and then cell fusion was performed using 50% polyethylene glycol 3350 (Sigma). Cells were suspended in HAT medium (RPMI1640 medium supplemented with ½×HT (MP), ½×HAT (MP), 10% FBS, 50 ng/L mouse IL-6, and 500 mg/mL D-Glucose), dispensed in a 96-well microculture plate and then cultured.

(4) ELISA

Culture supernatants of wells in which hybridomas had grown were collected, and then hybridomas producing monoclonal antibodies reactive to $rhVEGF_{165}$ were selected. $rhVEGF_{165}$ was diluted with PBS (−), dispensed into a 96-well ELISA plate (Nunc) at 1 μg/well, allowed to stand overnight at 4° C., and thus bound onto the plate surface. Next, after 3 times of washing with 350 μL of 0.05% Tween 20-containing PBS (−) (hereafter, denoted as "PBS-T"), 300 μL of 1% skim milk-containing PBS-T was dispensed into each well, followed by blocking at room temperature for 1 hour. After washing with PBS-T, the culture supernatant of the hybridomas was dispensed into an ELISA plate on which $rhVEGF_{165}$ had been immobilized, and then allowed to react for 1 hour at room temperature. After washing with PBS-T, 100 μL of peroxidase (hereafter, denoted as "POD")-labeled anti-mouse immunoglobulin antibody (BETHYL) diluted 10000-fold was dispensed into each well, and then allowed to react for 1 hour at room temperature. After similar washing was performed, a POD substrate that had been prepared to a concentration of 1 mg/mL POD was added, and then the resultant was allowed to develop color at room temperature for 5 minutes. The reaction was stopped with 1.5 N sulfuric acid, and then absorbance at 490 nm was measured using a plate reader (Molecular Devices).

(5) Establishment of Anti-VEGF Monoclonal Antibody

Based on the absorbance of a plate to which no rhVEGF$_{165}$ had been immobilized, wells each found to have an absorbance three or more times the baseline value were determined to be positive, and then cloning was performed by a limiting dilution method. Cell supernatants of wells containing single colonies were examined for antibody activity by the method of the above (4), isolated, and then cultured, thereby establishing a hybridoma cell line producing a monoclonal antibody reactive to rhVEGF$_{165}$. From the thus established hybridomas, two positive clones were selected, antibodies produced from these hybridomas were designated as KLHa505 and KLHb1501, respectively.

Example 2

Evaluation of the Capability of Monoclonal Antibodies to Inhibit Binding of VEGF to its Receptor An anti-VEGF antibody binds to VEGF to block the binding of VEGF to its receptors, VEGFR-1 and/or VEGFR-2, to be able to inhibit signal transduction through mediation of VEGF.

KLHa505 and KLHb1501 were separated and purified from the culture supernatants of the two positive clones using Protein G.

Next, IgG Fc-VEGFR-1 or IgG Fc-VEGFR2 was immobilized on a 96-well ELISA plate. After blocking with 2% bovine serum albumin, a purified antibody mixed with rhVEGF was added to the plate, followed by reaction at room temperature for 1 hour. A solution was prepared by mixing with rhVEGF, and then washed 3 times with 0.05% TWEEN® 20-containing TBS (TBS: 50 mM Tris-HCl (pH7.4), 500 mM NaCl; hereafter, referred to as "TBS-T"). Thereafter, through color development using rabbit anti-human VEGF polyclonal antibody-HRP, the rhVEGF content was determined.

As a result, it was demonstrated that the KLHa505 antibody competitively inhibits binding of VEGF to VEGFR-1 and VEGFR-2, and the KLHb1501 antibody competitively inhibits binding of VEGF to VEGFR-2 (FIG. 1).

That is, it was demonstrated in this Example that the antibodies of the present invention, KLHa505 and KLHb1501, can block VEGF-associated signal transduction.

Example 3

Measurement of Dissociation Constant of KLHa505 and KLHb1501 for Binding to rhVEGF With the use of BIAcore-3000, Kd of KLHa505 and Kd of KLHb1501 for binding to VEGF were determined. rhVEGF was immobilized on a CMS chip, serial dilution was performed twice with HBS-EP buffer, and then each antibody was injected at a flow rate of 30 µL/min. Kd is $K_{off}/K_{on}$.

As a result, it was demonstrated that the dissociation constant for binding of KLHa505 to rhVEGF was 4.23 pmol/L, and the dissociation constant for binding of KLHb1501 to rhVEGF was 0.60 pmol/L.

When compared with the dissociation constant for an existing antibody (for example, the dissociation constant for Avastin (bevacizumab) is 4.9 nmol/L), the dissociation constants for the antibodies of the present invention were each 1/1000 or less that for the existing antibody. Hence, the binding activity of the antibodies that bind to VEGF is significantly high.

That is, in this Example, the antibodies (high-affinity anti-VEGF antibodies) having extremely high affinity for VEGF were obtained.

Example 4

Examination of the Inhibiting Effect of the Monoclonal Antibodies, KLHa505 and KLHb1501 on HUVEC Proliferation It was examined if KLHa505 and KLH1501 inhibited VEGF activity exerted to normal human umbilical vein-derived endothelial cells (hereafter, referred to as "HUVEC"). HUVEC was used for the test to such an extent that the passage number did not exceed 8. With 1% fetal calf serum-containing Medium 200, 10000 cells each were seeded on a 96-well cell culture plate, rhVEGF was added at a final concentration of 50 ng/mL and KLHa505 or KLHb1501 was added at a final concentration of 2500 ng/mL each, cells were cultured for 24 hours, and then the numbers of cells were determined.

As a result, compared to positive controls (VEGF and isotype control antibody ("Control IgG" in FIG. 2)), cells with KLHa505 or KLHb1501 were found to exert a significant decrease in the number of cells (FIG. 2).

It was thus demonstrated in this Example that the high-affinity antibodies of the present invention can inhibit blood vessel-derived cells' cell proliferation activity due to VEGF, and can suppress angiogenesis.

Example 5

Examination of the In Vivo Inhibiting Effect of the Monoclonal Antibodies, KLHa505 and KLHb1501, on Cell Proliferation One lineage of human colon adenocarcinoma LS174T cells (about 1×10$^7$ cells) cryopreserved in liquid nitrogen were thawed in a warm bath at 37° C. two weeks before the experiment. Subsequently, to a 100-mm cell dish added with McCoy's 5A medium containing 10% fetal calf serum warmed in advance at 37° C., the thawed cell suspension was added, and then cells were grown to 80% confluency. Thereafter, cells were subcultured at 1:5, followed by 3 times of continuous subculturing. When all cells reached the number of cells required for inoculation, cells were removed from the dish using a 0.25% trypsin-EDTA solution, and then washed with PBS. Saline containing 50% MatriGel® was added to the washed cells to a concentration of 2×10$^7$/mL, and then the resultant was inoculated subcutaneously to the abdomen of each Balb/C nude mouse at 100 µL/mouse, specifically at 2×10$^6$ cells/mouse.

On the next day of cell inoculation, administration of KLHa505 and KLHb1501 was initiated. Regarding the dosage of KLHa505, administration was performed for 5 mouse per group, and thus (i) model control group (saline alone), (ii) 5 mg/kg KLHa505 group, (iii) 2.5 mg/kg KLHa505 group and (iv) 0.5 mg/kg KLHa505 group were prepared. Similar administration groups were prepared also for KLHb1501.

Regarding the administration method, KLHa505 or KLHb1501 dissolved in saline in an amount of 200 µL per mouse was administered once on day 2 and on day 5 in each week through intraperitoneal injection. To a model control group, 200 μL of saline was simultaneously administered by the same method.

Regarding the administration period, administration was continuously performed for 18 days for KLHa505 and 22 days for KLHb1501. When the antibodies were administered, the maximum diameter "a" and the minimum diameter "b" of a tumor nodule of each nude mouse were measured, and the tumor volume was calculated according to the formula $V=0.5 \times a \times b^2$.

As a result, KLHa505 and KLHb1501 were demonstrated to have capability of significantly inhibiting in vivo tumor growth (FIG. 3 and FIG. 4).

That is, this Example demonstrated that the high-affinity antibodies of the present invention are effective for treatment or prevention of a cancer.

Example 6

Determination of the Nucleotide Sequences and Amino Acid Sequences of Monoclonal Antibody Variable Regions mRNAs were extracted from hybridomas that produce KLHa505 and KLHb1501, cDNAs were prepared using reverse transcriptase. With the use of these cDNAs as templates, the nucleotide sequences of mouse IgG antibody heavy chain and light chain variable regions were amplified by PCR, and then the nucleotide sequences were analyzed, thereby the amino acid sequences of complementarity determining regions contained in the light chain and heavy chain variable regions were determined.

Furthermore, the amino acid sequences of CDR1, CDR2 and CDR3 of KLHa505 and KLHb1501 variable region were determined using IMGT/V-QUEST software, version 3.3.0, on the immunoglobulin database "the international ImMunoGeneTics information System®" (IMGT/GENE-DB).

The results are each shown in the following Table 1 and Table 2.

TABLE 1

| KLHa505 | |
|---|---|
| Heavy chain (V-D-J region) | |
| Nucleotide sequence | cagatccagttggtgcagtctggacctgagctgaagaagc ctggagagacagtcaagatctcctgcaaggcttctgggta taccttcacaaactatggaatgaactgggtgaagcaggct ccaggaaagggtttaaagtggatgggctggataaacacct acactggagagccaacatatcttgatgacttcaagggacg gtttgccttctctttggaaacctctgccagcactgcctac ttgcagatcaacaacctcaaaaatgaggacacgtctacat atttctgtgcaagattttcctacggtattacctggttctt cgatgtctggggcgcagggaccacggtcaccgtctcctca (SEQ ID NO: 33) |
| Peptide sequence | QIQLVQSGPELKKPGETVKISCKASGYTFTNYGMNWVKQA PGKGLKWMGWINTYTGEPTYLDDFKGRFAFSLETSASTAY LQINNLKNEDTSTYFCARFSYGITWFFDVWGAGTTVTVSS (SEQ ID NO: 34) |
| Light chain (V-J region) | |
| Peptide sequence | DIVMSQSPSSLAVSAGEKVTMSCKSSQSLLNSRTRKNYLA WYQQKPGQSPKLLIYWASTRESGVPDRFTGSGSGTDFTLT ISSVQAEDLAVYYCKQSYNLYTFGGGTKLEIK (SEQ ID NO: 36) |

TABLE 1-continued

| KLHa505 | |
|---|---|
| Sequence Heavy chain | |
| VH-CDR1 | GYTFTNYG (SEQ ID NO: 14) |
| VH-CDR2 | INTYTGEP (SEQ ID NO: 16) |
| VH-CDR3 | ARFSYGITWFFDV (SEQ ID NO: 18) |
| Light chain | |
| VL-CDR1 | QSLLNSRTRKNY (SEQ ID NO: 20) |
| VL-CDR2 | WAS |
| VL-CDR3 | KQSYNLYT (SEQ ID NO: 22) |

TABLE 2

| KLHb1501 | |
|---|---|
| Heavy chain (V-D-J region) | |
| Nucleotide sequence | gatgtgcagcttcaggagtcgggacctggcctggtgaaac cttctcagtctctgtccctcacctgcactgtcactggcta ctcaatcaccagtgattatgcctggacctggatccggcag tttccaggagacaaactggagtggatgggctacataagct acagtggtagcactcgctacaacccatctctcaaaagtcg aatctctatcactcgagacacatccaagaaccagttcttc ctgcacttgaattctgtgactactgaggacacggccacat atttctgtgcaagaggggggattactacggtagtcgccc ctggtttgcttactggggccaagggactctggtcactgtc tctgcag (SEQ ID NO: 37) |
| Peptide sequence | DVQLQESGPGLVKPSQSLSLTCTVTGYSITSDYAWTWIR QFPGDKLEWMGYISYSGSTRYNPSLKSRISITRDTSKNQ FFLHLNSVTTEDTATYFCARGGDYYGSRPWFAYWGQGTL VTVSA (SEQ ID NO: 38) |
| Light chain (V-J region) | |
| Peptide sequence | QAVVTQESALTTSPGETVTLTCRSSTGAVTISNYANWVQE KPDHLFTGLIGGTNNRAPDVPARFSGSLIGDKAALTITGA QTEDEAIYFCALWYSNHLVFGEGTKLTVL (SEQ ID NO: 40) |
| Sequence Heavy chain | |
| VH-CDR1 | GYSITSDYA (SEQ ID NO: 24) |
| VH-CDR2 | ISYSGST (SEQ ID NO: 26) |
| VH-CDR3 | ARGGDYYGSRPWFAY (SEQ ID NO: 28) |
| Light chain | |
| VL-CDR1 | TGAVTISNY (SEQ ID NO: 30) |
| VL-CDR2 | GTN |
| VL-CDR3 | ALWYSNHLV (SEQ ID NO: 32) |

Example 7

Preparation of Human-IgG1 Chimeric KLHa505 Antibody (KLHa505HC Antibody)

From the hybridoma that produces the KLHa505 antibody, the KLHa505 antibody heavy chain variable region gene (nucleotide sequence: SEQ ID NO: 33, amino acid sequence: SEQ ID NO: 34) and light chain variable region gene (nucleotide sequence: SEQ ID NO: 35, amino acid sequence: SEQ ID NO: 36) were cloned. Next, these genes were each ligated in-frame to the nucleotide sequence of the human IgG1 heavy chain constant region gene or light chain (κ chain) constant region gene. PCR was carried out using a primer having the 5'-terminal nucleotide sequence of the heavy chain variable region, Kozak sequence, and a restriction enzyme Mlu I sequence and an antisense primer having a complementary sequence of the 3'-terminal nucleotide sequence and a restriction enzyme Nhe I sequence. Next, PCR was carried out using a primer having the 5'-terminal nucleotide sequence of the light chain variable region gene and a restriction enzyme BamH I sequence, and an antisense primer having a complementary sequence of the 3'-terminal nucleotide sequence and a restriction enzyme BsiW I sequence. The thus obtained amplification product was treated with restriction enzymes Mlu I and Nhe I or BamH I and BsiW I, and then the resultant was incorporated into the Mlu I-Nhe I site of the human IgG1 heavy chain constant region expression plasmid (pEF6/G1) or the BamH I-BsiW I site of the human Ig light chain (κ chain) constant region expression plasmid (pEF1/G1k). In pEF6/G1, the human IgG1 heavy chain constant region gene (nucleotide sequence: SEQ ID NO: 41, amino acid sequence: SEQ ID NO: 42) was cloned into the plasmid pEF6/myc-His (Invitrogen). In pEF1/G1-k, the human Ig light chain (κ chain) constant region gene (nucleotide sequence: SEQ ID NO: 43, amino acid sequence: SEQ ID NO: 44) was cloned into the plasmid pEF1/myc-His (Invitrogen). The mouse heavy chain variable region and the human heavy chain constant region were linked by a restriction enzyme Nhe I, and the mouse light chain variable region and the human light chain constant region were linked by a restriction enzyme BsiW I sequence.

The plasmids pEF6/G1-KLHa505 and pEF1/G1-K-KLHa505 were introduced into 293F cells using a FreeStyle™ 293 Expression System (Thermo Fisher Scientific K.K.), and thus the human IgG1 chimeric KLHa505 antibody (hereafter, may also be referred to as "KLHa505HC antibody") was transiently expressed. Next, the KLHa505HC antibody was purified from a culture supernatant of 293F cells, into which the chimeric gene had been introduced, using Protein G Sepharose 4 Fast Flow (GE Healthcare Japan). A solvent was substituted with D-PBS (−) using an Amicon Ultra-15 centrifugal filter unit (Merck millipore). The concentration of the purified KLHa505HC antibody was determined using Nano drop 1000 (Thermo Fisher Scientific K.K.). Binding of the KLHa505HC antibody to VEGF was evaluated by the method described in the above "Purification of monoclonal antibody (4) ELISA". As a result, specific binding of the KLHa505HC antibody to VEGF was confirmed.

That is, in this Example, the chimeric antibody of the high-affinity anti-VEGF antibody of the present invention was obtained.

Example 8

Preparation of Human-IgG1 Chimeric KLHb1501 Antibody (KLHb1501HC Antibody)

From hybridomas that produce the KLHb1501 antibody, the KLHb1501 antibody heavy chain variable region gene (nucleotide sequence: SEQ ID NO: 37, amino acid sequence: SEQ ID NO: 38) and light chain variable region gene (nucleotide sequence: SEQ ID NO: 39, amino acid sequence: SEQ ID NO: 40) were cloned. Next, these genes were each ligated in-frame to the nucleotide sequence of a human IgG1 heavy chain constant region gene or light chain (λ chain) constant region gene. PCR was carried out using a primer having the 5' terminal nucleotide sequence of the heavy chain variable region, Kozak sequence, and a restriction enzyme Xho I sequence, and an antisense primer having the complementary sequence of the 3' terminal nucleotide sequence and a restriction enzyme Nhe I sequence. Next, PCR was carried out using a primer having the 5' terminal nucleotide sequence of the light chain variable region gene and a restriction enzyme EcoR I sequence, and an antisense primer having the complementary sequence of the 3' terminal nucleotide sequence and a restriction enzyme Avr II sequence. The thus obtained amplification products were treated with restriction enzymes Xho I and Nhe I, or EcoR I and Avr II, and then incorporated into the Xho I-Nhe I site of a human IgG1 heavy chain constant region expression plasmid (pFUSE-CHIg-hG1; InvivoGen), or the EcoR I-Avr II site of a human Ig light chain (λ chain) constant region expression plasmid (pFUSE2ss-CLIg-hl2: InvivoGen). In pFUSE-CHIg-hG1, the human IgG1 heavy chain constant region gene (nucleotide sequence: SEQ ID NO: 41, amino acid sequence: SEQ ID NO: 42) was cloned. In pFUSE2ss-CLIg-hl2, the human Ig light chain (λ chain) constant region gene (nucleotide sequence: SEQ ID NO: 43, amino acid sequence: SEQ ID NO: 44) was cloned. The mouse heavy chain variable region and the human heavy chain constant region were linked by the restriction enzyme Nhe I, and the mouse light chain variable region and the human light chain constant region were linked by the restriction enzyme Avr II sequence.

Example 9

In Vivo Inhibiting Effect of Human IgG1 Chimeric KLHb1501 Antibody (KLHb1501HC Antibody) on Tumor Growth Human colon cancer cell line LS174T cells were subcutaneously injected at a rate of $2 \times 10^6$ cells per mouse into the right flanks of the 20 immunodeficient mice. On the next day of injection, 0.9% NaCl (control group A) or KLHb1501HC antibody (control group B) was intraperitoneally administered. The KLHb1501HC antibody was administered to the mice of control group B twice a week at 0.5 mg/Kg, 2.5 mg/Kg, or 5 mg/Kg. Furthermore, similarly to the antibody, 0.9% NaCl was administered twice a week to the mice of control group A. On days 1, 5, 8, 12, 15, 19 and 22 after inoculation of cells, tumor sizes were measured, and then tumor volumes were calculated using the formula: V (mm$^3$) =(d: minor axis)$^2$×(D: major axis)/2. The results are shown in FIG. 5. In FIG. 5, group A (0.9% NaCl control) is indicated with (◇), group B (mice injected with the anti-VEGF antibody) is indicated with (□: 0.5 mg/Kg), (△: 2.5 mg/Kg), or (○: 5.0 mg/Kg). As shown in FIG. 5, significant decreases in tumor volume were observed in mice injected with the KLHb1501HC antibody. These results demonstrated that the KLHb1501HC antibody; that is an antibody of the present invention, inhibited (suppressed) the tumor growth even in vivo. This demonstrated that a pharmaceutical composition comprising the human IgG1 chimeric anti-VEGF antibody of the present invention is significantly effective for treatment or prevention of cancer.

Example 10

Preparation of Canine-IgGB Chimeric KLHa505 Antibody (KLHa505CC Antibody)

From the hybridoma that produces the KLHa505 antibody, the KLHa505 antibody heavy chain variable region gene (nucleotide sequence: SEQ ID NO: 33, amino acid sequence: SEQ ID NO: 34) and light chain variable region gene (nucleotide sequence: SEQ ID NO: 35, amino acid sequence: SEQ ID NO: 36) were cloned. Next, these genes were each ligated in-frame to the nucleotide sequence of the canine IgGB heavy chain constant region gene or light chain (κ chain) constant region gene. PCR was carried out using a primer having the 5'-terminal nucleotide sequence of the heavy chain variable region, Kozak sequence, and a restriction enzyme EcoR V sequence, and an antisense primer having a complementary sequence of the 3'-terminal nucleotide sequence and a restriction enzyme Nhe I sequence. Next, PCR was carried out using a primer having the 5'-terminal nucleotide sequence of the light chain variable region gene and a restriction enzyme EcoR I sequence, and an antisense primer having a complementary sequence of the 3'-terminal nucleotide sequence and a restriction enzyme Xho I sequence. The thus obtained amplification product was treated with restriction enzymes Eco V and Nhe I, or EcoR I and Xho I, and then the resultant was incorporated into the EcoR V-Nhe I site of a canine IgGB heavy chain constant region expression plasmid (pFUSE2ss-CHIg-dGB), or the EcoR I-Xho I site of a canine Ig light chain constant region expression plasmid (pFUSE2ss-CHIg-dK). In pFUSE2ss-CHIg-dGB, the canine IgGB heavy chain constant region gene (nucleotide sequence: SEQ ID NO: 45, amino acid sequence: SEQ ID NO: 46) was cloned into plasmid pFUSE2ss-CLIg-hl2 (InvivoGen). In pFUSE2ss-CHIg-dK, the canine Ig light chain (κ chain) constant region gene (nucleotide sequence: SEQ ID NO: 47, amino acid sequence: SEQ ID NO: 48) was cloned into plasmid pFUSE2ss-CLIg-hl2. The mouse heavy chain variable region and the canine heavy chain constant region were linked by the restriction enzyme Nhe I sequence, and the mouse light chain variable region and the canine light chain constant region were linked by the restriction enzyme Xho I sequence.

Example 11

Preparation of Canine-IgGB Chimeric KLHb1501 Antibody (KLHb1501CC Antibody)

From hybridomas that produce the KLHb1501 antibody, the KLHb1501 antibody heavy chain variable region gene (nucleotide sequence: SEQ ID NO: 37, amino acid sequence: SEQ ID NO: 38) and light chain variable region gene (nucleotide sequence: SEQ ID NO: 39, amino acid sequence: SEQ ID NO: 40) were cloned. Next, these genes were each ligated in-frame to the nucleotide sequence of a canine IgGB heavy chain constant region gene or light chain (λ chain) constant region gene. PCR was carried out using a primer having the 5' terminal nucleotide sequence of the heavy chain variable region, Kozak sequence, and a restriction enzyme EcoR V sequence, and an antisense primer having the complementary sequence of the 3' terminal nucleotide sequence and a restriction enzyme Nhe I sequence. Next, PCR was carried out using a primer having the 5' terminal nucleotide sequence of the light chain variable region gene and a restriction enzyme EcoR I sequence and an antisense primer having the complementary sequence of the 3' terminal nucleotide sequence and a restriction enzyme Sca I sequence. The thus obtained amplification products were treated with restriction enzymes Eco V and Nhe I, or EcoR I and Sca I, and then incorporated into the EcoR V-Nhe I site of a canine IgGB heavy chain constant region expression plasmid (pFUSE2ss-CHIg-dGB) or the EcoR I-Sca I site of a canine Ig light chain constant region expression plasmid (pFUSE2ss-CHIg-dK). In pFUSE2ss-CHIg-dGB, the canine IgGB heavy chain constant region gene (nucleotide sequence: SEQ ID NO: 45, amino acid sequence: SEQ ID NO: 46) was cloned to plasmid pFUSE2ss-CLIg-hl2 (InvivoGen). In pFUSE2ss-CHIg-dK, the canine Ig light chain (λ chain) constant region gene (nucleotide sequence: SEQ ID NO: 49, amino acid sequence: SEQ ID NO: 50) was cloned into plasmid pFUSE2ss-CLIg-hl2. The mouse heavy chain variable region and the canine heavy chain constant region were linked by the restriction enzyme Nhe I, and the mouse light chain variable region and the canine light chain constant region were linked by the restriction enzyme Sca I sequence.

Example 12

Cross-Reactivity of Canine-IgGB Chimeric KLHb1501 Antibody (KLHb1501CC Antibody) to Human VEGF165 and Canine VEGFA Whether or not the thus prepared canine-IgGB chimeric antibody had capability of binding to human VEGF165 and canine VEGFA (VEGF164) was confirmed by ELISA. Human VEGF165 or canine VEGFA were diluted with TBS, dispensed to a 96-well ELISA plate (Nunc) at 20 ng per well, and then incubated at 37° C. for 1 hour for binding to the plate surface. Next, after 3 times of washing with 300 μL of 0.02% Tween 20-containing PBS (−) (hereafter, denoted as "PBS-T"), 300 μL of 3% skim milk-containing PBS (−) was dispensed into each well, followed by blocking at 37° C. for 1 hour. After washing with PBS-T, the canine-IgGB chimeric KLHb1501 antibody (KLHb1501CC antibody) serially diluted from the concentration of 1 μg/ml was dispensed to an ELISA plate to which VEGF had been immobilized, and then allowed to react at 37° C. for 1 hour. After washing with PBS-T, a peroxidase-labeled anti-canine immunoglobulin antibody (BETHYL) prepared to have a concentration of 100 ng/ml was dispensed at 100 μL per well, and then allowed to react at 37° C. for 1 hour. After washing similarly, TMB Single Solution was added for color development at room temperature. After the reaction was stopped with 1 N sulfuric acid, absorbance at 450 nm was measured using a plate reader (Molecular Devices). The results are shown in FIG. 6. It was demonstrated that the KLHb1501CC antibody binds to canine VEGFA with the same degree of affinity as that to human $VEGF_{165}$.

These results demonstrated that a pharmaceutical composition comprising the canine IgGB chimeric anti-VEGF antibody of the present invention can be used for treatment or prevention of diseases of dogs.

Example 13

In Vivo Inhibiting Effect of Canine IgGB Chimeric KLHb1501 Antibody (KLHb1501CC Antibody) on Tumor Growth in Human Cancer Cell Line Human colon cancer cell line LS174T cells were subcutaneously injected at a rate of $2\times10^6$ cells per mouse to the right flanks of 20 immunodeficient mice. On the next day of injection, 0.9% NaCl (control group A) or the KLHb1501CC antibody (control group B) was administered intraperitoneally. The KLHb1501CC antibody was administered twice a week to the mice of control group B at 0.5 mg/Kg, 2.5 mg/Kg, or 5 mg/Kg. Furthermore, similarly to the antibody, 0.9% NaCl was administered twice a week to the mice of control group A. On days 5, 8, 12, 15, 19 and 22 after inoculation of cells, tumor sizes were measured and tumor volumes were calculated using the formula: V (mm³)=(d:

minor axis)$^2$×(D: major axis)/2. The results are shown in FIG. 7. In FIG. 7, group A (0.9% NaCl control) is indicated with (■), group B (mice injected with the anti-VEGF antibody) is indicated with (●: 0.5 mg/Kg), (▲: 2.5 mg/Kg), or (Δ: 5.0 mg/Kg). As shown in FIG. 7, significant decreases in tumor volume were observed in mice injected with the KLHb1501CC antibody.

These results demonstrated that the KLHb1501CC antibody of the present invention also inhibits (suppresses) in vivo the growth of human tumors. These results also demonstrated that a pharmaceutical composition comprising the canine IgGB chimeric anti-VEGF antibody of the present invention is significantly effective for treatment or prevention of cancer.

Example 14

In Vivo Inhibiting Effect of Canine IgGB Chimeric KLHb1501 Antibody (KLHb1501CC Antibody) on Tumor Growth in Canine Cancer Cell Line Canine bone sarcoma cell line D-17 cells were subcutaneously injected at a rate of 1×10$^7$ cells per mouse to the right flanks of 20 immunodeficient mice. After the mean tumor volume reached 150 mm$^3$, 0.9% NaCl (control group A) or the KLHb1501CC antibody (control group B) was intraperitoneally administered. The KLHb1501CC antibody was administered twice a week to the mice of control group B at 0.5 mg/Kg, 2.5 mg/Kg, or 5 mg/Kg. Similarly to the antibody, 0.9% NaCl was administered twice a week to the mice of control group A. On days 50, 54, 57, 61, 64, 67, 70, 74, 77 and 81 after inoculation of cells, tumor sizes were measured, and the tumor volumes were calculated using the formula: V (mm$^3$)=(d: minor axis)$^2$×(D: major axis)/2. The results are shown in FIG. 8. In FIG. 8, group A (0.9% NaCl control) is indicated with (■), and group B (mice injected with the anti-VEGF antibody) is indicated with (●: 0.5 mg/Kg), (▲: 2.5 mg/Kg), or (Δ: 5.0 mg/Kg). As shown in FIG. 8, significant decreases in tumor volume were observed in mice injected with the KLHb1501CC antibody.

These results demonstrated that the KLHb1501CC antibody of the present invention inhibits (suppresses) the growth of tumors of dogs even in vivo. These results also demonstrated that a pharmaceutical composition comprising the canine IgGB chimeric anti-VEGF antibody of the present invention is significantly effective for treatment or prevention of cancer of dogs.

Example 15

Examination of the Antigen Binding Site of the Antibody of the Present Invention To examine the binding site of the antibody of the present invention in VEGF, a binding experiment based on the ELISA method was conducted as follows.

In this Example, as anti-VEGF antibodies, three anti-VEGF antibodies including KLHa505HC and KLHb1501HC obtained in Examples 7 and 8 were used.

Furthermore, as VEGF, three types of VEGF, (i) VEGF165 containing exon 8a that is the C-terminal region of VEGF, (ii) VEGF121 lacking heparin binding region, and (iii) VEGF165b having an amino acid sequence (exon 8b) differing from the C-terminal region of VEGF165 were used.

The binding experiment was specifically conducted as follows.

Human VEGF165 (consisting of exon 1, 2, 3, 4, 5, 7 and 8a), human VEGF165b (consisting of exon 1, 2, 3, 4, 5, 7 and 8b) or human VEGF121 (consisting of exon 1, 2, 3, 4, 5 and 8a) was diluted with TBS, dispensed to a 96-well ELISA plate (Nunc) at 20 ng per well, and then incubated at 37° C. for 1 hour, for binding onto the plate surface. Next, after 3 times of washing with 300 μL of 0.02% Tween 20-containing PBS (−) (hereafter, denoted as "PBS-T"), 300 μL of 3% skim milk-containing PBS (−) was dispensed to each well, followed by blocking at 37° C. for 1 hour. After washing with PBS-T, the KLHa505HC antibody or KLHb1501HC antibody serially diluted from the concentration of 1 μg/ml was dispensed to an ELISA plate to which VEGF had been immobilized, and then allowed to react at 37° C. for 1 hour. After washing with PBS-T, a peroxidase-labeled anti-human immunoglobulin antibody (BETHYL) prepared to have a concentration of 100 ng/ml was dispensed at 100 μL per well, and then allowed to react at 37° C. for 1 hour. After washing similarly, TMB Single Solution was added for color development at room temperature. After the reaction was stopped with 1 N sulfuric acid, absorbance at 450 nm was measured using a plate reader (Molecular Devices).

As a result, all of the three anti-VEGF antibodies including KLHa505HC and KLHb1501HC that is the anti-VEGF antibody of the present invention were found to bind to all of VEGF$_{165}$, VEGF$_{121}$ and VEGF$_{165}$b above (FIG. 9, 10).

The result demonstrates that the antibody of the present invention binds to exon 1 to 5 regions of VEGF.

INDUSTRIAL APPLICABILITY

According to the present invention, novel antibodies capable of binding to VEGF with significantly high affinity compared to the prior art can be provided.

Sequence Listing Free Text
    SEQ ID NO: 13: synthetic DNA
    SEQ ID NO: 14: synthetic peptide
    SEQ ID NO: 15: synthetic DNA
    SEQ ID NO: 16: synthetic peptide
    SEQ ID NO: 17: synthetic DNA
    SEQ ID NO: 18: synthetic peptide
    SEQ ID NO: 19: synthetic DNA
    SEQ ID NO: 20: synthetic peptide
    SEQ ID NO: 21: synthetic DNA
    SEQ ID NO: 22: synthetic peptide
    SEQ ID NO: 23: synthetic DNA
    SEQ ID NO: 24: synthetic peptide
    SEQ ID NO: 25: synthetic DNA
    SEQ ID NO: 26: synthetic peptide
    SEQ ID NO: 27: synthetic DNA
    SEQ ID NO: 28: synthetic peptide
    SEQ ID NO: 29: synthetic DNA
    SEQ ID NO: 30: synthetic peptide
    SEQ ID NO: 31: synthetic DNA
    SEQ ID NO: 32: synthetic peptide
    SEQ ID NO: 33: synthetic DNA
    SEQ ID NO: 34: synthetic peptide
    SEQ ID NO: 35: synthetic DNA
    SEQ ID NO: 36: synthetic peptide
    SEQ ID NO: 37: synthetic DNA
    SEQ ID NO: 38: synthetic peptide
    SEQ ID NO: 39: synthetic DNA
    SEQ ID NO: 40: synthetic peptide
    SEQ ID NO: 41: synthetic DNA
    SEQ ID NO: 42: synthetic peptide
    SEQ ID NO: 43: synthetic DNA
    SEQ ID NO: 44: synthetic peptide SEQ ID NO: 45: synthetic DNA
SEQ ID NO: 46: synthetic peptide
SEQ ID NO: 47: synthetic DNA
SEQ ID NO: 48: synthetic peptide
SEQ ID NO: 49: synthetic DNA
SEQ ID NO: 50-54: synthetic peptide

The invention claimed is:

1. A monoclonal antibody against VEGF, or an antigen-binding fragment thereof, that binds to a vascular endothelial growth factor (VEGF), comprising:

CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18; and CDR-L1 that comprises the amino acid sequence of SEQ ID NO: 20, CDR-L2 that comprises the amino acid sequence of Trp-Ala-Ser, and CDR-L3 that comprises the amino acid sequence of SEQ ID NO: 22.

2. The monoclonal antibody, or the antigen-binding fragment thereof, according to claim 1, wherein the monoclonal antibody inhibits binding of a vascular endothelial growth factor (VEGF) to at least one receptor selected from the group consisting of vascular endothelial growth factor receptor-1 (VEGFR1) and vascular endothelial growth factor receptor-2 (VEGFR2).

3. The monoclonal antibody, or the antigen-binding fragment thereof, according to claim 1, wherein the monoclonal antibody is a chimeric antibody, a humanized antibody, or a caninized antibody.

4. The antibody, or the antigen-binding fragment thereof, according to claim 1, further comprising a heavy chain constant region comprising an amino acid sequence derived from a human IgG1 heavy chain constant region and a light chain constant region comprising an amino acid sequence derived from a human IgG1 light chain constant region.

5. The antibody, or the antigen-binding fragment thereof, according to claim 4, wherein the amino acid sequence derived from a human IgG1 heavy chain constant region comprises the amino acid sequence of SEQ ID NO: 42, and the amino acid sequence derived from a human IgG1 light chain constant region comprises the amino acid sequence of SEQ ID NO: 44.

6. The antibody, or the antigen-binding fragment thereof, according to claim 5, comprising:

a heavy chain that comprises the amino acid sequence of SEQ ID NO: 34, and the amino acid sequence of SEQ ID NO: 42; and a light chain that comprises the amino acid sequence of SEQ ID NO: 36, and the amino acid sequence of SEQ ID NO: 44.

7. The antibody, or the antigen-binding fragment thereof, according to claim 1, further comprising a heavy chain constant region comprising an amino acid sequence derived from a canine IgGB heavy chain constant region and a light chain constant region comprising an amino acid sequence derived from a canine Ig light chain (κ chain) constant region or a canine Ig light chain (λ chain) constant region.

8. The antibody, or the antigen-binding fragment thereof, according to claim 7, wherein an amino acid sequence derived from a canine IgGB heavy chain constant region comprises the amino acid sequence of SEQ ID NO: 46, an amino acid sequence derived from a canine Ig light chain (κ chain) constant region comprises the amino acid sequence of SEQ ID NO: 48, and an amino acid sequence derived from a canine Ig light chain (λ chain) constant region comprises the amino acid sequence of SEQ ID NO: 50.

9. The antibody, or the antigen-binding fragment thereof, according to claim 8, comprising:
a heavy chain that comprises the amino acid sequence of SEQ ID NO: 34 and the amino acid sequence of SEQ ID NO: 46; and
a light chain that comprises the amino acid sequence of SEQ ID NO: 36 and the amino acid sequence of SEQ ID NO: 48 or 50.

10. The antigen-binding fragment according to claim 1, wherein the antigen-binding fragment is a single-chain antibody or a double-chain antibody.

11. A hybridoma that produces the monoclonal antibody according to claim 1.

12. A pharmaceutical composition comprising the monoclonal antibody, or the antigen-binging fragment thereof, according to claim 1; and a pharmaceutically acceptable carrier.

13. A kit comprising the monoclonal antibody, or the antigen-binding fragment thereof, according to claim 1; and a buffer, an enzyme solution, a secondary antibody, a solution for dilution, and/or instructions.

14. A method for treating a VEGF-mediated cancer or a VEGF-mediated eye disease in a subject in need thereof, comprising a step of administering a therapeutically effective amount of the antibody, or the antigen-binding fragment thereof, according to claim 1 to the subject.

15. The method according to claim 14, wherein the therapeutically effective amount inhibits angiogenesis or vascular hyperpermeability.

16. The method according to claim 15, wherein the angiogenesis is pathological angiogenesis.

17. The method according to claim 14, wherein the cancer is a solid cancer.

18. The method according to claim 14, wherein the cancer is selected from the group consisting of colorectal cancer, rectal cancer, breast cancer, non-small-cell lung cancer, non-Hodgkin's lymphoma (NHL), renal cell cancer, prostate cancer, liver cancer, pancreas cancer, soft tissue sarcoma, Kaposi's sarcoma, carcinoid tumor, head and neck cancer, melanoma, ovarian cancer, and mesothelioma.

19. The method according to claim 14, wherein the VEGF-mediated eye disease is at least one selected from age-related macular degeneration, diabetic retinopathy, diabetic macular edema, neovascular glaucoma, retinal vein occlusion, retinopathy of prematurity, choroidal neovascularization associated with pathological myopia, pterygium, rubeosis, pannus, Stevens-Johnson syndrome, and an immunological rejection in a transplanted tissue of the eye.

20. The monoclonal antibody, or an antigen-binding fragment thereof, of claim 1, comprising a heavy chain comprising the amino acid sequence of SEQ ID NO: 34 and a light chain comprising the amino acid sequence of SEQ ID NO: 36.

21. The monoclonal antibody, or an antigen-binding fragment thereof, of claim 20, wherein the antibody, or antigen-binding fragment thereof, binds to the vascular endothelial growth factor (VEGF) with a dissociation constant of $1 \times 10^{-11}$ mol/L or less.

* * * * *